United States Patent
El-Agnaf

(10) Patent No.: US 10,548,984 B2
(45) Date of Patent: Feb. 4, 2020

(54) RVG DERIVED PEPTIDES

(71) Applicant: United Arab Emirates University, Al Ain (AE)

(72) Inventor: Omar M. Ali El-Agnaf, Morecambe (UA)

(73) Assignee: United Arab Emirates University, Al Ain (AE)

( * ) Notice: Subject to any disclaimer, the term of this patent is extended or adjusted under 35 U.S.C. 154(b) by 132 days.

(21) Appl. No.: 15/549,031

(22) PCT Filed: Feb. 4, 2015

(86) PCT No.: PCT/IB2015/050846
§ 371 (c)(1),
(2) Date: Aug. 4, 2017

(87) PCT Pub. No.: WO2016/124976
PCT Pub. Date: Aug. 11, 2016

(65) Prior Publication Data
US 2018/0028675 A1    Feb. 1, 2018

(51) Int. Cl.
*A61K 47/64*     (2017.01)
*A61K 31/713*    (2006.01)
*C07K 14/005*    (2006.01)
*C12N 7/00*      (2006.01)

(52) U.S. Cl.
CPC .......... *A61K 47/64* (2017.08); *A61K 31/713* (2013.01); *C07K 14/005* (2013.01); *C12N 7/00* (2013.01); *C12N 2760/20122* (2013.01); *C12N 2760/20133* (2013.01); *C12N 2760/20171* (2013.01)

(58) Field of Classification Search
None
See application file for complete search history.

(56) References Cited

U.S. PATENT DOCUMENTS

| | | | | |
|---|---|---|---|---|
| 2005/0255097 A1* | 11/2005 | Reid | ............... | A61K 35/58 424/94.64 |
| 2009/0156470 A1 | 6/2009 | Chatterton | | |
| 2009/0176729 A1* | 7/2009 | Tan | ............... | C12N 15/113 514/44 R |
| 2010/0233084 A1* | 9/2010 | Narasimhaswamy | ... | B82Y 5/00 424/9.1 |
| 2012/0122956 A1* | 5/2012 | Pastorino | ............. | A61K 31/437 514/44 A |
| 2012/0171201 A1* | 7/2012 | Sapra | ............... | A61K 31/44 424/133.1 |
| 2013/0143909 A1* | 6/2013 | Chong | ............... | C08G 65/329 514/283 |

FOREIGN PATENT DOCUMENTS

| | | | |
|---|---|---|---|
| CN | 102250222 A | | 11/2011 |
| WO | WO 2005023849 | * | 3/2005 |
| WO | 2008054544 A2 | | 5/2008 |
| WO | 2011019763 A2 | | 2/2011 |
| WO | 2011087804 A2 | | 7/2011 |
| WO | 2012027558 A2 | | 3/2012 |

OTHER PUBLICATIONS

NIH "Creutzfeldt-Jakob Disease Fact Sheet" accessed from ninds.nih.gov on Feb. 12, 2019 (Year: 2019).*
European Search Report, European Application No. 15881004.4, dated Jun. 12, 2018, 8 pages.
Gao, Yikun, et al., "RVG-Peptide-Linked Trimethylated Chitosan for Delivery of siRNA to the Brain," Biomacromolecules, 2014, 15, 1010-1018.
Gong, Cheng, et al., "Target Delivery of a Gene Into the Brain Using the RVG29-oligoarginine Peptide." Biomaterials, 33: 3456-3463 (2012).
Zimmermann, Tracy S. et al., RNAi-mediated gene silencing in non-human primates, Nature, vol. 441, May 4, 2006, 5 pages.
Kumar, Priti et al., Transvascular delivery of small interfering RNA to the central nervous system, Nature, vol. 448, Jul. 5, 2007, 7 pages.
International Search Report and Written Opinion of the International Searching Authority for International Application No. PCT/IB2015/050846, dated Mar. 16, 2015, 9 pages.
Monville C, et al., Comparison of incremental and accelerating protocols of the rotarod test for the assessment of motor deficits in the 6-OHDA model, Journal of Neuroscience Methods, vol. 158(2), dated Dec. 15, 2006, 12 pages.
European Examination Report, European Application No. 15881004A, dated Jun. 26, 2019, 5 pages.

* cited by examiner

*Primary Examiner* — Adam Weidner
(74) *Attorney, Agent, or Firm* — Fitch, Even, Tabin & Flannery, LLP

(57) ABSTRACT

The invention relates to short RVG derived peptides for use in delivering therapeutic agents across the blood brain barrier and to target cells, for example those cells in the central nervous system. The invention provides method and compositions to treat diseases, such as neurodegenerative diseases, with therapeutic agents associated with targeting peptides.

17 Claims, 17 Drawing Sheets
(9 of 17 Drawing Sheet(s) Filed in Color)
Specification includes a Sequence Listing.

| Peptide | Sequence |
|---|---|
| PEPTIDE (SEQ ID NO:2) | CDIFTNSRGK |
| RI-PEPTIDE (SEQ ID NO:3) | kGrsntfidc |
| TEST-PEPTIDE (SEQ ID NO:4) | CDIFTNSRGKGGGGrrrrrrrr |
| TEST RI-PEPTIDE (SEQ ID NO:5) | rrrrrrrr-Sar-Sar-Sar-Sar-kGrsntfidc |
FIGURE 1
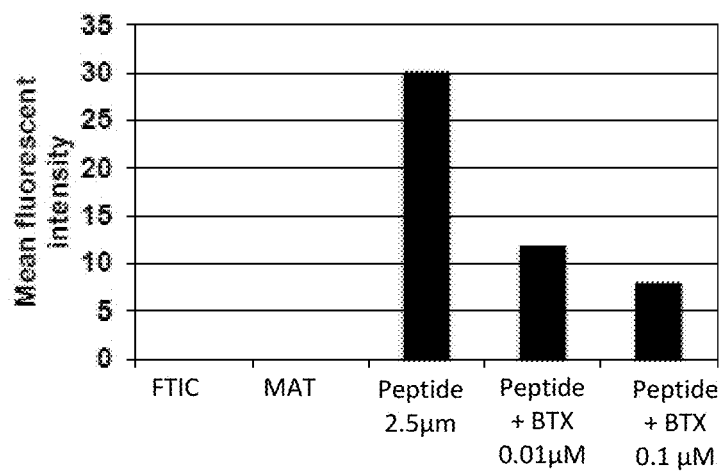
FIGURE 2A
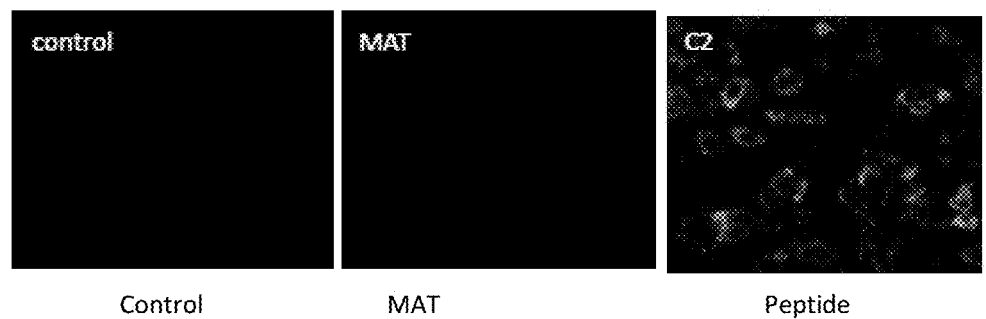
FIGURE 2B

SEQUENCE LISTING

<160> NUMBER OF SEQ ID NOS: 14

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Sarcosine
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 1

Xaa Xaa Xaa Xaa Xaa Xaa Xaa Xaa Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Asp Ile Phe Thr Asn Ser Arg Gly Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(10)
<223> OTHER INFORMATION: D-amino acid

<400> SEQUENCE: 3

Lys Gly Arg Ser Asn Thr Phe Ile Asp Cys
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(23)
<223> OTHER INFORMATION: D-amino acid

<400> SEQUENCE: 4

Cys Asp Ile Phe Thr Asn Ser Arg Gly Lys Gly Gly Gly Gly Arg Arg
1               5                   10                  15

Arg Arg Arg Arg Arg Arg

```
<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-amino acid
<220> FEATURE:
<221> NAME/KEY: MOD_RES
<222> LOCATION: (10)..(13)
<223> OTHER INFORMATION: Sarcosine
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(23)
<223> OTHER INFORMATION: D-amino acid

<400> SEQUENCE: 5

Arg Arg Arg Arg Arg Arg Arg Arg Arg Xaa Xaa Xaa Xaa Lys Gly Arg
1               5                   10                  15

Ser Asn Thr Phe Ile Asp Cys
            20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6 agagggguguu cucuauguat t                                          21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
cucuauguag guuccaaatt                                             20

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: This sequence may encompass 5-11 residues
```

```
<400> SEQUENCE: 8

Arg Arg Arg Arg Arg Arg Arg Arg Arg Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(9)
<223> OTHER INFORMATION: This sequence may be composed of L-Arg or D-Arg
      residues

<400> SEQUENCE: 9

Arg Arg Arg Arg Arg Arg Arg Arg Arg
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Sarcosine

<400> SEQUENCE: 11

Xaa Xaa Xaa Xaa
1

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 12

Gly Gly Gly Gly Gly Gly Gly Gly Gly Gly
1               5                   10

<210> SEQ ID NO 13
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Arg Arg Arg Arg Arg Arg
1               5

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Arg Arg Arg Arg Arg Arg Arg Arg Arg Arg
1               5                   10
```

RVG DERIVED PEPTIDES

SEQUENCE LISTING

The instant application contains a Sequence Listing which has been submitted electronically in ASCII format and is hereby incorporated by reference in its entirety. Said ASCII copy, created on Aug. 25, 2017, is named 9194-141485-US_SL.txt and is 4,804 bytes in size.

TECHNICAL FIELD

This invention is directed to short peptides derived from the rabies virus glycoprotein (RVG), and the use of those peptides for the delivery of agents into targeted cells. In particular the invention relates to the delivery of small interfering RNA (siRNAs) across the blood brain barrier (BBB).

BACKGROUND

A number of approaches have been proposed to target delivery of agents to cells and in particular to deliver agents across the blood brain barrier. Being able to deliver agents across the blood brain barrier is useful when treating CNS and neurodegenerative diseases.

The use of RNAi therapy such as siRNA for treating CNS diseases such as neurodegenerative diseases has been proposed. However problems with siRNA therapy for CNS diseases include: 1) siRNAs do not cross BBB, which is composed of tight junctions formed by endothelial cells surrounding the brain; and 2) they are not stable in the presence of serum nucleases.

Zimmerman et al (2006) reports complexing siRNA to liposomes to protect the siRNA from serum degradation and facilitate their uptake by the endocytic pathway. However liposomal methods may induce toxicity in neuronal cells.

Kumar et al (2007) and WO 2008/054544 disclose the use of a RVG peptide for targeting cells and delivering agents across the blood brain barrier. RVG-29 peptide specifically binds to the acetylcholine receptor (AchR) found on neuronal cells; however its relatively large size makes the peptide immunogenic and more susceptible to proteolytic degradation.

The invention aims to provide peptides that can be used for delivering agents to cells.

SUMMARY OF INVENTION

This invention relates to peptides for delivering agents to cells. The invention relates to peptides comprising the sequence CDIFTNSRGK (SEQ ID NO:2) or kGrsntfidc (SEQ ID NO:3). One aspect of the invention comprises a peptide having the structure:
$A^1$-B-C or C-B-$A^2$, wherein B is optionally present or absent and wherein:
$A^1$ comprises the sequence CDIFTNSRGK (SEQ ID NO:2);
$A^2$ comprises the sequence kGrsntfidc (SEQ ID NO:3);
B is a linker sequence; and
C is a cell penetrating peptide (CPP) sequence.

In one embodiment of the invention the peptide has the sequence of CDIFTNSRGKGGGGrrrrrrrrr (SEQ ID NO:4).

In another embodiment of the invention the peptide has the sequence of rrrrrrrrr-Sar-Sar-Sar-Sar-kGrsntfidc (SEQ ID NO:5).

The cell penetrating peptide sequence can be an arginine rich sequence such as a polymeric arginine residue of various lengths. For example the polymeric arginine residue may be 5-11 arginine residues in length (SEQ ID NO: 8). Preferably the cell penetrating peptide is a polymeric arginine residue being 9 arginines in length (SEQ ID NO: 9). Preferably the arginine residues are D-arginine residues. More preferably the cell penetrating peptide comprises 9 D-arginine residues (SEQ ID NO: 9).

The peptide does not comprise the full length RVG-29 peptide. The peptide has a sequence shorter than the RVG-29 peptide, preferably the peptide sequences of $A^1$ and $A^2$ are less than 15 residues. More preferably the peptide sequences of $A^1$ and $A^2$ are less than 12 residues. Preferably the peptide sequences of $A^1$ and $A^2$ are from 12 to 6 residues. Most preferably the peptide sequences of $A^1$ and $A^2$ are 10 residues in length.

The linker sequence may be a glycine or sarcosine sequence. Preferably the linker sequence is Gly-Gly-Gly-Gly (SEQ ID NO: 10) or Sar-Sar-Sar-Sar (SEQ ID NO: 11).

The peptide can be used as a delivery molecule for an agent in the treatment of a disease. Therefore a further aspect of the invention relates to a composition comprising a delivery peptide comprising a sequence $A^1$-B-C or C-B-$A^2$, as described above, and an agent associated with the peptide. Preferably the agent is a therapeutic agent, a diagnostic agent or an imaging agent.

In one embodiment the agent can be a nucleic acid or nucleic acid derivative or analogue thereof, for example, but not limited to DNA or RNA. The RNA may be siRNA, miRNA, tRNA, strand template RNA (stRNA), short hair pin RNA (shRNA) or analogues or combinations thereof. In a preferred embodiment the agent is an RNA interference molecule. Preferably the agent is siRNA. More preferably the agent is α-synuclein siRNA. The siRNA may comprise the sequence of SEQ ID NO:6.

The peptide can be used for the targeted delivery of molecules in gene therapy. Preferably for the delivery of siRNA against CNS disorders.

In one embodiment the composition can be used as a medicament. The composition may be used in the treatment of central nervous system disorders, neurological disorders or neurodegenerative diseases. Preferably the composition is used in the treatment of synucleinopathies, more preferably in the treatment of Parkinson's disease.

A further aspect of the invention comprises a pharmaceutical composition comprising a peptide having a structure $A^1$-B-C or C-B-$A^2$, as described above, associated with an agent, and a pharmaceutically acceptable carrier or diluent. Preferably the agent is a therapeutic agent, a diagnostic agent or an imaging agent. More preferably the agent is siRNA.

Another aspect of the invention relates to a method of delivering an agent to a cell, the method comprising contacting the cell with a composition as described above. In one embodiment the agent may be a therapeutic agent, a diagnostic agent or an imaging agent as described above.

The cell may be an in vitro cell or a cell in a subject. The cell may be a central nervous system cell. Examples of cells include but are not limited to neuron, glial cells and endothelial cells of the blood brain barrier.

The composition may be administered to the cell by intranasal, subcutaneous, parenteral, intrathecal, intracranial or intravenous administration.

A further aspect of the invention comprises a method of treating a central nervous system disorder, neurological disorder or neurodegenerative disease in a subject. The method can comprise administering to the subject a composition comprising a delivery peptide having the structure $A^1$-B-C or C-B-$A^2$, as described above, and an agent associated with the peptide. Preferably the neurodegenerative disorder is Parkinson's disease.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows the sequences of the peptides according to the invention;

FIGS. 2A and 2B show the results of the competitive binding assay between the biotinylated-peptide (SEQ ID NO:2) and BTX to nAchRs present on M17 cells (FIG. 2A) and the immunocytochemistry analysis of the M17 cells incubated with or without biotinylated-peptide (FIG. 2B);

FIGS. 12A and 12 B show the results of Th staining of the SNpc (FIG. 12A) and straitum (FIG. 12B) from mice treated with peptide/siRNA complexes and MPTP or saline: (FIG. 12A) Means±SEM for 5 mice per group. p=0.0001 (*) by one-way ANOVA for multiple comparison. *p<0.001 by Newman-Kauls post-hoc analysis to test individual groups against MPTP treated group.

DETAILED DESCRIPTION OF THE INVENTION

Figure 3:
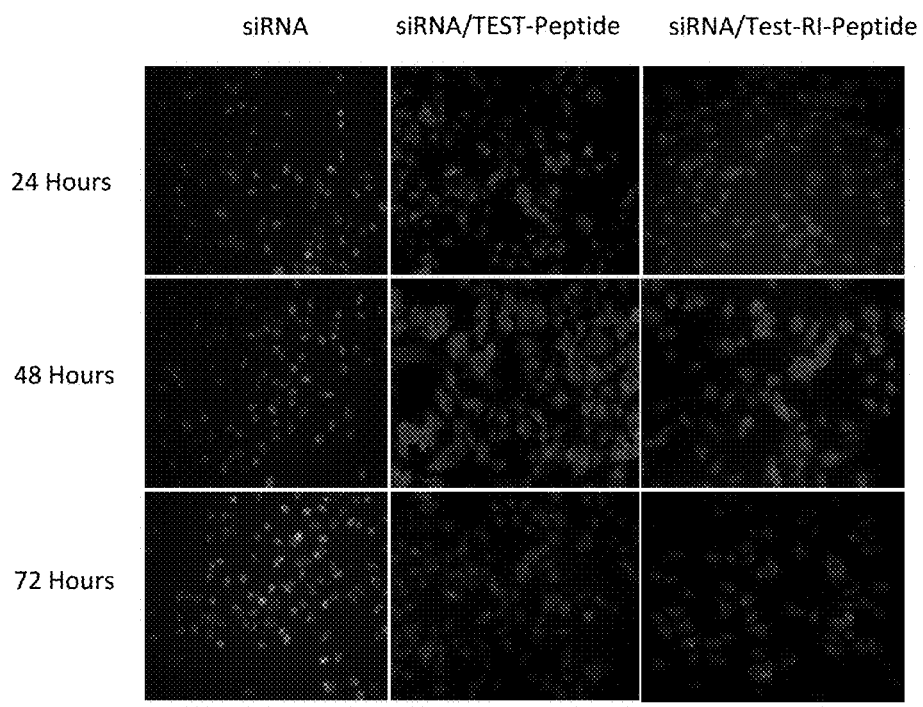
FIG. 3 shows the results of M17 cells treated with the peptides complexed to siRNA labelled with rhodamine or treated with siRNA-rhodamine alone. Images of the rhodamine-siRNA (red) positive cells are shown with the nuclei stained with DAPI (blue)

This invention relates to peptides for delivering agents to cells. The inventors have surprisingly discovered that peptides having the sequence of CDIFTNSRGK (SEQ ID NO:2) or kGrsntfidc (SEQ ID NO:3) can bind to the AchR and can be used to facilitate the transport of other agents across the blood brain barrier (BBB) and into cells.

The peptides can bind to the acetyl choline receptors present on the surface of a cell, enabling targeted delivery to acetyl choline receptor expressing cells. Furthermore the peptide can cross the BBB to enable binding to cells within the brain, for example to neurons.

Accordingly the invention provides a peptide comprising a first peptide sequence comprising the sequence CDIFTNSRGK (SEQ ID NO:2) or kGrsntfidc (SEQ ID NO:3). The peptide for delivery of an agent to a cell may further a second peptide sequence comprising a cell penetrating peptide sequence. The peptide may optionally comprise a linker sequence between the first peptide sequence and the cell penetrating peptide sequence.

In one embodiment of the invention the peptides have the following structure:
$A^1$-B-C or C-B-$A^2$, wherein B is optionally present or absent.
$A^1$ comprises the sequence CDIFTNSRGK (SEQ ID NO:2)
$A^2$ comprises the sequence kGrsntfidc (SEQ ID NO:3).
B is a linker sequence.
C is a cell penetrating peptide (CPP) sequence.

$A^1$ and $A^2$ are RVG derived peptide sequences comprising the sequence CDIFTNSRGK (SEQ ID NO:2) or kGrsntfidc (SEQ ID NO:3) or derivative or variant thereof. By RVG derived peptide it is meant a peptide sequence comprising a fragment of the RVG peptide, or a retro inverse sequence of such a fragment. The RVG derived peptide does not comprise the full length of the RVG peptide. Preferably the RVG derived peptide $A^1$ or $A^2$ is less than 15 residues in length. More preferably the peptide sequences $A^1$ or $A^2$ are from 12 to 6 residues.

The delivery peptide may have amino acids in the L- and/or D-configuration. As is conventional nomenclature, wherein the one letter code is lower case this indicates that the amino acid has the "D" configuration. Throughout this specification reference will be made to lower case amino acid codes or codes proceeded by "(D)-" and these shall both be taken as equivalent.

Variants of SEQ ID NO: 2 and SEQ ID NO:3 are also encompassed by the invention. A variant of the RVG derived peptides, SEQ ID NO:2 and SEQ ID NO:3, refers to a peptide substantially similar in structure and function, i.e. has the ability to pass through the BBB. A variant of the RVG derived peptides, SEQ ID NO:2 and SEQ ID NO:3, can include naturally-occurring, synthetic, recombinant or chemically modified polypeptides. Variants include conservative or non-conservative amino acid changes to the reference sequences.

The term "conservative substitution," refers to a change in the amino acid composition of the polypeptide that does not substantially alter the polypeptide's activity. For example, a conservative substitution refers to substituting an amino acid residue for a different amino acid residue that has similar chemical properties. Conservative substitution tables providing functionally similar amino acids are well known in the art and include for example replacement of a leucine with an isoleucine or valine, an aspartate with a glutamate, or a threonine with a serine. Conservative substitutions also include individual substitutions, deletions or additions of amino acids to the reference sequences. These conservative substitutions that alter, add or delete a single amino acid or a small number of amino acids to the sequence can also be considered variants with the scope of the invention if the change still maintains the activity of the peptide (i.e. the ability of an RVG peptide variant to penetrate the BBB).

The term derivative also refers to peptides which have been chemically modified, for example but not limited to by techniques such as ubiquitination, labelling, pegylation or addition of other molecules.

In one embodiment the invention provides a delivery peptide comprising the sequence of CDIFTNSRGK (SEQ ID NO:2). When the delivery peptide comprises the sequence CDIFTNSRGK (SEQ ID NO:2) the peptide preferably has the structure $A^1$-B-C. Preferably $A^1$ has a length of 12 or less residues. In a preferred embodiment $A^1$ is a 10 residue length peptide having the sequence of CDIFTNSRGK (SEQ ID NO:2).

The peptides can also include non-naturally occurring amino acids, including non-native amino acids, substituted amino acids or one of more D-amino acids. Therefore the invention also includes peptides comprising modified amino acids.

Therefore the invention also provides a retro-inverso peptide, comprising D-amino acids, based on the sequence of CDIFTNSRGK (SEQ ID NO:2). The delivery retro-inverse peptide can comprise the sequence kGrsntfidc (SEQ ID NO:3). As the skilled person would understand SEQ ID NO:3 can also be referred to as D-Lys-Gly-D-Arg-D-Ser-D-Asn-D-Thr-D-Phe-D-Ile-D-Asp-D-Cys.

When the peptide comprises the sequence of kGrsntfidc (SEQ ID NO:3) the peptide preferably has the structure C-B-$A^2$. Preferably $A^2$ has a length of 12 residues or less. In a preferred embodiment $A^2$ is a 10 residue length peptide having the sequence of kGrsntfidc (SEQ ID NO:3).

The retro inverse peptide is considered to increase the stability of the peptide in vivo and in vitro and to make the peptide less susceptible to proteolytic degradation. Reversing the primary sequence and replacing the L-amino acids with D-amino acids can increase the peptide stability in vivo and increase the blood brain barrier permeability, whilst still maintaining the stereochemical dispositions of the side chains with respect to each other.

The linker sequence can be any suitable linker sequence. The linker will be of length such that it does not interfere with the translocation of the peptide across the cell membrane. When a linker sequence is present, B is preferably a plurality of glycine or sarcosine residues. The linker may be 1-10 amino acids in length. In one embodiment the linker can consist of a peptide of formula $G_x$ (SEQ ID NO: 12) or $Sar_x$ (SEQ ID NO: 1), where x is 1, 2, 3, 4, 5, 6, 7, 8, 9 or 10. More preferably the linker sequence is 4 residues long, for example Gly-Gly-Gly-Gly (SEQ ID NO: 10) or Sar-Sar-Sar-Sar (SEQ ID NO: 11). However other linker sequences and/or other lengths can be used.

When the peptide has the structure $A^1$-B-C, preferably the linker sequence comprises glycine residues. When the peptide has the structure C-B-$A^2$, preferably the linker sequence comprises sacrosine residues. The glycine and sacrosine residues act as linkers between the RVG derived peptide and the cell penetrating peptide sequence.

Preferably the cell penetrating peptide sequence is an arginine rich sequence of variable length. More preferably the cell penetrating peptide sequence is a polymeric arginine residue. The polymeric arginine residue may be 5-11 residues in length (SEQ ID NO: 8), i.e. 5, 6, 7, 8, 9, 10 or 11 residues. Preferably the polymeric arginine residue is a 9-arginine sequence (SEQ ID NO: 9).

Other arginine rich peptides can also be used as the cell penetrating peptide sequence. The arginine residues in the arginine sequence can be L-arginine, D-arginine or a mixture of L- and D-arginines. Preferably the residues in the arginine sequence are D-arginine, i.e. a 9r sequence (SEQ ID NO: 9).

Accordingly a most preferred peptide has the sequence CDIFTNSRGKGGGGrrrrrrrrr (SEQ ID NO:4) or rrrrrrrrr-Sar-Sar-Sar-Sar-kGrsntfidc (SEQ ID NO:5).

The invention further provides the peptides of the invention associated with an agent. Associating the agent with a peptide of the invention facilitates the delivery of the agent into the brain. The peptide can be used as a carrier to deliver agents across the BBB and to the targeted cells. In particular the peptides of the invention are useful as targeting moieties for selectively targeting cells expressing the acetylcholine receptor.

The agent can include but is not limited to therapeutic agents, diagnostic agents and imaging agents. Preferably the agent is a therapeutic agent. Therapeutic agents that are the most suitable for using with the peptides of this invention are those agents that are required to perform their pharmacological effect in the brain.

The agent associated with a peptide of the invention is preferably a nucleic acid or analogue or derivative thereof. The nucleic acid may be RNA or DNA. RNA includes but is not limited to siRNA, shRNA, miRNA, mRNA, and RNA, or combinations thereof. Preferably the agent is siRNA.

A nucleic acid or analogue or derivative thereof, includes nucleic acid sequences with modified nucleic acid residues. Any modified residue, derivative or analog may be used to the extent that it does not eliminate or substantially reduce activity (by at least 50%) of the nucleic acid, for example does not substantially reduce the RNAi activity of the RNA molecule.

The term "RNAi" refers to interfering RNA or RNA interference molecules that are RNA-based molecules that inhibit or down regulate gene expression. RNAi can be used to posttranscriptionally silence gene expression and RNA-interference molecules, include but are not limited to, unmodified and modified RNA molecules such as, small interfering RNA (siRNA), shorthair pin RNA (shRNA), micro RNA (miRNA), and double stranded DNA (dsDNA). "Short interfering RNA" (siRNA), can also be referred to as "small interfering RNA" and is a nucleic acid that has the ability to inhibit or reduce expression of a target gene.

A composition comprising the peptide may comprise a plurality of different agents associated with the peptide. For example, the composition may comprises a plurality of different siRNA agents associated with the peptide, where the siRNA agents silence different gene targets, and/or are targeted to different regions on the same gene.

The term "associated with" in reference to association between the peptide and the agent, means that one of the moieties is in physical association or contact with the other. The two moieties may be directly or indirectly linked, such that ability of the peptide to cross the BBB also assists the agent to cross the BBB and to cross cell membranes.

Where there is an indirect linkage the association between the agent and the CPP sequence of the peptide occurs via a further linker moiety. Linker moieties can include but are not limited to nucleic acid or peptide linker molecules. A direct linkage includes a chemical or a physical interaction between the two moieties. Example of direct interactions include non-covalent interactions, hydrophobic/hydrophilic, ionic, van der waals, or hydrogen bonding, and chemical bonding, including the formation of a covalent bond.

Preferably the association between the agent and the peptide are directly linked. More preferably the two moieties are electrostatically associated with each other. The type of association between the agent and the peptide will depend on the type of agent being used and the type of CPP sequence. For example when the agent is siRNA and the CPP sequence is a polyarginine sequence the positively charged arginine residues of the cell permeable peptide sequence can bind to the negatively charged siRNA by charge interactions.

The invention further provides a method for delivering an agent to a cell. The method comprising contacting the cell with a composition comprising an agent associated with a delivery peptide as described above.

The cells delivered a composition comprising the delivery peptide and associated agent can be part of a subject (i.e. in vivo) for example for therapeutic, diagnostic or prophylactic purposes. The cells can also be ex vivo cells, a biological sample or cultured cells (i.e. in vitro), for example as part of an assay.

The invention also relates to a method of treating a condition in a subject, preferably a human, comprising administering to the subject a composition comprising a delivery peptide associated with a therapeutic agent in an effective amount. The composition can be administered in a therapeutically effective amount.

The therapeutic agent to be delivered will depend on the condition being treated. The invention is particularly useful for targeting delivery of agents to central nervous system cells, in particular those cells located within the BBB. Cells that are targeted for delivery of an agent may have an acetylcholine receptor present on their surface. Cells of the central nervous system that may be targeted include but are not limited to neurons, glial cells and endothelial cells of the blood brain barrier.

In one embodiment the therapeutic agent is for treating a condition selected from a central nervous system disorder, neurological disorders or neurodegenerative diseases. Preferably the conditions is a synucleinopathies, for example Parkinson's disease.

It is suggested that levels of α-synuclein protein are involved in the pathogenesis of Parkinson's disease. The silencing of wild-type α-synuclein with RNAi molecules, such as siRNA, is proposed as an approach for treating Parkinson's disease and other synucleinopathies. Therefore the invention further provides a method of treating synucleinopathies, such as Parkinson's disease in a patient. Other synucleinopathies suitable for treatment with the invention include dementia with Lewy bodies (DLB) and multiple system atrophy (MSA). The method comprises administering to a subject an effective amount of a peptide of the invention associated with an α-synuclein siRNA molecule.

Without being bound by theory the peptide will facilitate transport of the associated siRNA molecule across the BBB, introducing the siRNA molecule into the brain cells and enabling the siRNA molecule to downregulate α-synuclein gene expression, and thereby reducing the levels of α-synuclein in the subject.

Due to the ability of the peptide and associated agent to cross the BBB and for the peptide to bind acetylcholine receptor expressing cells, the peptide can be used to target delivery of the therapeutic agent to the area where the intended pharmacological effect should take effect.

The terms "treating" and "treatment" is intended to include curing, reversing, alleviating, palliative and prophylactic treatment of the condition.

A "therapeutically effective amount" of a compound is an amount of the compound, which when administered to a subject, is sufficient to confer the intended therapeutic effect. A therapeutically effective amount can be given in one or more administrations.

The composition comprising the peptide and agent may be administered with other therapeutic agents. Such agents may be administered sequentially, simultaneously or concomitantly.

The invention also relates to a pharmaceutical composition comprising a delivery peptide having the structure $A^1$-B-C or C-B-$A^2$ as described above and an agent associated with the peptide, and a pharmaceutically acceptable excipient, such as diluents or carrier. The pharmaceutical composition may comprise additional therapeutic agents. The pharmaceutical composition may be formulated for intranasal, subcutaneous, parenteral, intrathecal, intracranial, intracerebral, intravenous or oral administration.

Suitable composition forms include forms suitable for oral administration such as tablets, capsule, pills, powders, sustained release formulations, solutions, and suspension; for parenteral injection such as sterile saline solutions, suspensions or emulsion.

Exemplary parenteral administration forms include suspensions or solutions in sterile aqueous solutions, for example aqueous propylene glycol or dextrose solutions. Such dosage forms can be suitably buffered, if desired.

Suitable pharmaceutical carriers include inert diluents or fillers, water and various organic solvents. Compositions may also include additional ingredients such as flavouring, binders, and excipients. Tablets may include: disintegrates such as starch, alginic acid and complex silicates; binding agents such as sucrose, gelatine and acacia, and lubricating agents such as magnesium stearate, sodium lauryl sulphate and talc.

Solid compositions may also include soft and hard gelatin capsules. Preferred materials include lactose, milk sugars and high molecular weight polyethylene glycols.

Aqueous suspensions or elixirs may include sweetening or flavouring agents, colours and dyes, emulsifying agents, suspending agents as wells as diluents such as water, ethanol, propylene glycol, glycerin or combinations thereof.

Pharmaceutical forms suitable for the delivery of the compounds of the present invention and methods of preparing the various pharmaceutical compositions will be readily apparent to those skilled in the art.

Preferably the peptide is formulated for delivery to the brain. Due to the ability of the peptides of the invention to cross the BBB and deliver the agent to the target cells, it is not necessary that that the peptide is administered locally to the site of need in the brain.

Using the peptides of the inventions as delivery molecules for agents enables targeting of the agents to cells in need of the agent thereof. The peptides also enable the delivery of the agents to sites distal from the site of administration, enabling systemic delivery of the agents to the CNS. In particular the delivery peptides of the invention enable non-invasive administration of siRNA into the CNS for treatment of central nervous system disorders and neurodegenerative diseases.

The invention also provides peptides more stable and less immunogenic that previously provided RVG delivery based peptide sequence. The peptides of the invention are also easier and cheaper to produce.

The invention is now described by way of example.

EXAMPLES

Peptides and siRNAs

Peptides having the sequence of CDIFTNSRGK (SEQ ID NO:2), kGrsntfidc (SEQ ID NO:3; RI-peptide), H-CDIFTNSRGKGGGGrrrrrrrrr (SEQ ID NO:4; Test-peptide) and H-rrrrrrrrr-Sar-Sar-Sar-Sar-kGrsntfidc (SEQ ID NO:5; Test-RI-peptide) were used in the experiments. A RVG-linker-9dR peptide, designated RVG-9R, as described in Kumar et al (2007) peptide comprising the 29 residue RVG peptide sequence was used as a comparison.

The peptides were synthesized by Shanghai Hanhong Chemical Co., Ltd (Shanghai, China) and EZBiolab (Carmel, USA).

siRNA against human α-synuclein (5'-3':AGAGGGUGUUCUCUAUGUAtt) (SEQ ID NO:6) and mouse α-synuclein (5'-3':CUCUAUGUAGGUUCCAAAtt) (SEQ ID NO:7) was synthesized by Ambion Applied Biosystems (Foster City, USA). FITC labelled siRNA was prepared using the Label IT siRNA Tracker intralocalization kit (Mirus Bio LLC, Madison, USA). For each labelling reaction, 30 µg of siRNA was mixed with 10 µl of the 10× labelling buffer and 10 µl of Label IT siRNA Tracker reagent and incubated overnight at 37° C. Rhodamine labelled siRNA was synthesized using PlatinumBright™ Nucleic Acid Labelling Kit (Kreatech) according to manufacturer's instructions. Briefly, 2 µl of siRNA (100 pmol), 8.9 µl of ULS dye rhodamine and 2 µl of 10× labelling solution were mixed together and incubated overnight at 37° C. following which the extra unlabelled rhodamine was removed by KREA pure columns. To verify the integrity of the siRNA after labelling, the labelled siRNA was run on a 2% gel for 15 mins at 50V.

Primary Culture

M17 cell lines stably overexpressing wild type α-synuclein were a gift from Dr. Mark Cookson (Laboratory of Neurogenetics, NIH). The cells were cultured in Dulbecco's MEM containing 10% fetal bovine serum, 1% penicillin-streptomycin, 2 mM freshly prepared glutamine and 50 µg/ml of G418. All cells were maintained at 37° C. in a humidified incubator with 5% $CO_2$ and used for a maximum of 20 passages.

Preparation of Cell Lysates

Cells were dissociated from culture plates and transferred into a culture tube with 10 ml of DMEM (containing 10% fetal bovine serum, 1% penicillin-streptomycin, and 2 mM freshly prepared glutamine), and then centrifuged for 10 min at 225 RCF. The pellet was lysed in 1 ml of sigma Cellytic™ containing a cocktail of protease inhibitors. The cell lysate was keep at room temperature for 1 hr before overnight incubation at −80° C. The next day, the cell lysate was thawed and centrifuged for 20 mins at 15,000 RCF. The supernatant was collected for SDS-PAGE and western blot analysis.

Animals

Male C57BL/6 mice (8-16 weeks old), bred at the Central Animal Facility of the UAE University were used. All animals were maintained in an air-conditioned room with controlled temperature (24±2° C.) and humidity (55±15%) under a 12 h light/dark cycle. The animals were given food and water ad libitum. All procedures were performed in accordance with the National Institutes of Health guidelines for the use of live animals and were approved by Institutional Animal Ethics Committee of the College of Medicine and Health Sciences, United Arab Emirates University.

Imaging

Light microscopic analysis was performed using a Zeiss Axiovert 40 CFL inverted microscope (Carl Zeiss, Germany) equipped with a Zeiss AxioCam HRc camera and Axiovision 4.8 software. Confocal images were obtained using a Nikon Eclipse C1 plus confocal microscope (Nikon) and EZC1 3.90 acquisition and analysis software.

Statistical Analysis

All values are expressed as mean±SEM, unless otherwise mentioned. Differences among means were analyzed using one-way analysis of variance (ANOVA). When ANOVA showed significant differences, pair-wise comparisons between means were tested by Newman-Keuls post-hoc testing. In all analysis, the null hypothesis was rejected when p was greater than 0.05.

Example 1—Binding of Peptides to Neuronal Cells In Vitro

To confirm that the binding specificity of the peptide to the neuronal cells was mediated by its binding to nAchRs, a competition assay was performed using alpha bangarotoxin (BTX) peptide, which is a competitive antagonist for nAchRs.

M17 cells were incubated with the biotinylated-peptide (SEQ ID NO:2) (2.5 µM) in the absence or presence of BTX peptide (0.01 µM or 0.1 µM) at 4° C. for 1 hr, stained with avidin-FITC and analyzed by FACS.

Immunocytochemistry was used to confirm the binding of the peptide (SEQ ID NO:2) to M17 cells. M17 cells were incubated with or without biotinylated-peptides (SEQ ID NO:2) or with the MAT peptide which served as a negative control. The cells were then stained with avidin-FITC and viewed by fluorescence microscopy.

BTX inhibited peptide binding to M17 cells in a dose-dependent manner FIG. 2A. Peptides bound to nAchRs were clustered on the surface of M17 cells FIG. 2B. Cells incubated with the peptide (SEQ ID NO:2) showed FITC-positive immunostaining indicating that the peptide binds specifically to neuronal cells, and its binding is mediated by nAchRs present on neuronal cells.

Example 2—Stability of Peptides In Vivo

Figure 13:
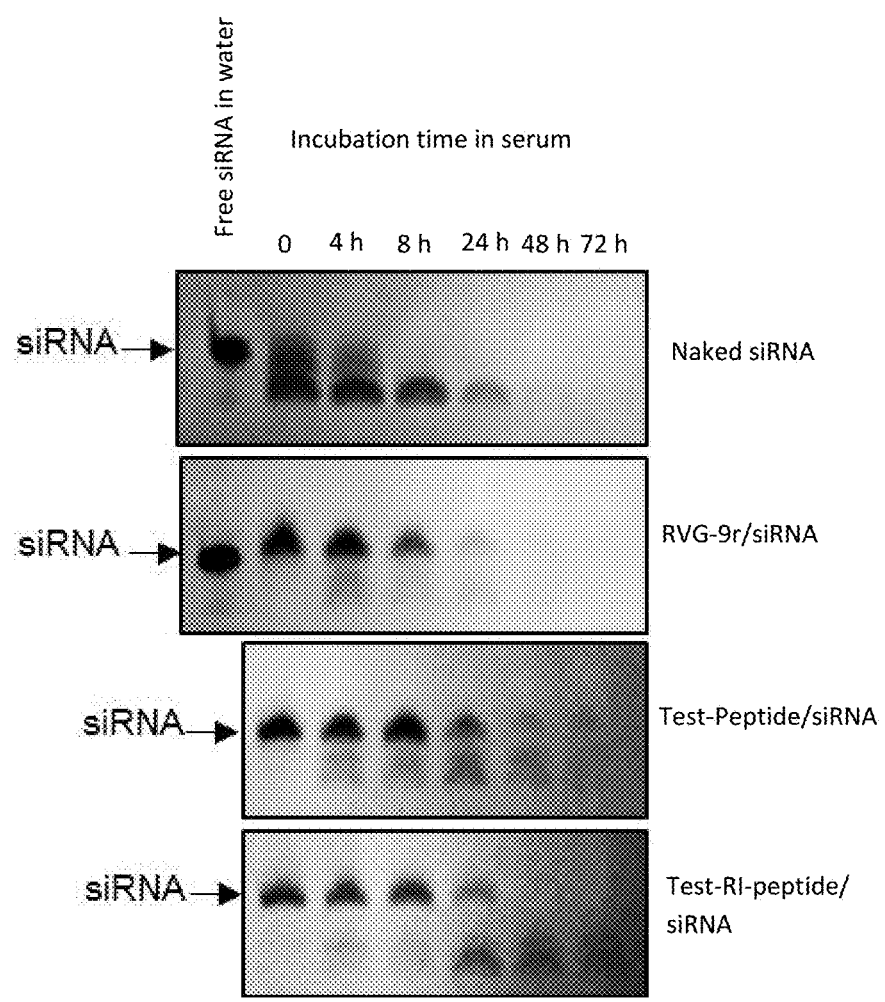
FIG. 13 shows the results of the stability assays of peptide-siRNA complexes in serum. Naked and peptide-complexed siRNA were incubated on 50% mouse serum at 37° C. and aliquots taken at indicated time-points were digested with proteinase K and then analysed. Free siRNA in water was included as control. The position of intact, uncomplexed siRNA is indicated.

To analyse siRNA integrity in the presence of serum nuclease, naked siRNA or siRNA/peptide complexes (80 pmol) were incubated at 37° C. in 50% mouse serum for up to 72 hours. siRNA complexed with the RVG-9r peptide was included as a control. Aliquots taken at various time points (0 min, 2 hours, 8 hours, 24 hours, 48 hours, and 72 hours) were digested with proteinase K (2 mg/ml, Sigma Aldrich) for 1 hours and frozen in 2× urea-TBE loading buffer. Samples were analysed for the presence of intact siRNA on 15%-urea-polyacrylamide gels in TBE buffer and visualised on a UV-transilluminator subsequent to ethidium, bromide staining (FIG. 13).

Naked siRNA was rapidly degraded by serum nucleases and RVG-9r complexed with siRNA was only partially stable for up to 8 hours in the presence of serum. Both the test peptides retained siRNA integrity for at least 8 hours and enables partial protection of siRNA for up to 24 hours. These results show that the Test-peptide (SEQ ID NO:4) and TEST-RI-peptide (SEQ ID NO:5) vectors improved the stability of the siRNA and enabled intact siRNA to be detected for up to 24 hours in serum. The test peptides are more resistant to proteolytic degradation than the longer RVG-9r peptide and therefore can be used to confer enhanced protection of siRNA from serum nucleases.

Example 3—siRNA Uptake and Gene Silencing In Vitro

To test for the ability of the peptides to transfect siRNA into neuronal cells. M17 cells stably expressing wild-type α-synuclein were transduced with rhodamine labelled siRNA designed specifically to target α-synuclein that were complexed with the Test-peptide (SEQ ID NO:4) or Test-RI-peptide (SEQ ID NO:5) at a molar ratio of 1:40.

Uptake of siRNA into cells was monitored using rhodamine-labelled siRNA. siRNA-Rhod (100 pmol) was complexed with the peptides in serum-free DMEM for 15 min at room temperature. The complexes were then added to M17 cells (plated at $20 \times 10^4$ cells per well in 6-well plates on the previous day). After incubation for 4 h at 37° C., 10% fetal bovine serum was added to the medium and the cells were cultured for a further 48-72 h. After 24, 48 and 72 hours of transfection the cells were fixed and the intracellular localisation of siRNA was confirmed using florescence microscopy.

For gene silencing experiments, M17 cells stably over-expressing wild type α-synuclein were incubated with 100 pmol of siRNA complexed with the peptides at a molar ratio of 40:1 (peptide: siRNA). The expression levels of α-synuclein protein was analyzed at 48 h and 72 h post transduction by Western blot.

To visualize peptide uptake by cells M17 cells were incubated with biotinylated-peptides at room temperature for 1 h and then washed three times with blocking buffer (1% BSA in 0.1M PBS). Avidin conjugated to FITC was added to the cells and incubated at room temperature for 20 min followed by further washes with blocking buffer after which the cells were fixed with 4% paraformaldehyde-PBS solution (pH 7.2) for 30 min at room temperature. The cells were washed once more with PBS and mounted for viewing by confocal microscopy.

For Western blot analysis of protein expression after siRNA transfection of cells, cell lysates were separated by NuPAGE Bis-Tris 4-12%, 1 mm gel and transferred onto a nitrocellulose membrane. The membranes were probed with anti-α-syn antibody (211, Santa Cruz Biotechnology) and β-actin antibody (Santa Cruz Biotechnology). α-Synuclein expression was normalized by beta-actin. The protein bands were visualized using Super signal west pico chemiluminescent substrate (Pierce) and the band intensities determined using Quantity One-4.1.1 software (Bio-Rad) and Image J.

Following transfection with TEST-peptide/siRNA or TEST-RI-peptide/siRNA complexes, a punctate pattern of fluorescence was observed in the cytoplasm, indicating the entry of siRNA-rhodamine into the cells. The diffuse distribution of labelled siRNA suggests that siRNA complexes escaped the endocytotic mechanism. Following 48-72 hrs, fluorescence appeared to accumulate in more discrete areas of the cytoplasm. These results indicate that the siRNA was successfully transfected by the peptides into M17 cells. 72 h post-transfection most of the rhodamine signals decreased and only a faint signal was observed, FIG. 3.

Figure 4A:
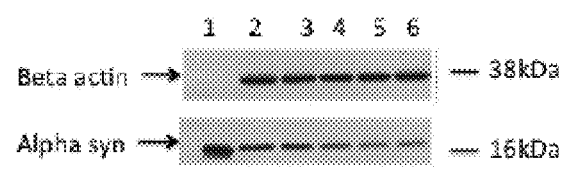
FIGS. 4A and 4B show α-synuclein expression evaluated by western blotting for proteins extracted from M17 cells stably expressing wild-type α-synuclein at (FIG. 4A) 48 hours and (FIG. 4B) 72 hours after transfection with α-synuclein siRNA complexed with the peptides. Lane 1: recombinant α-synuclein; lane 2: untreated cells; Lane 3: cells transfected with scrambled siRNA by commercial media (negative control); Lane 4: siRNA transfected by RVG-9r; Lane 5: siRNA transfected by test-peptide (SEQ ID NO:4); Lane 6: siRNA transfected by Test-RI-peptide (SEQ ID NO:5)
Figure 4B:
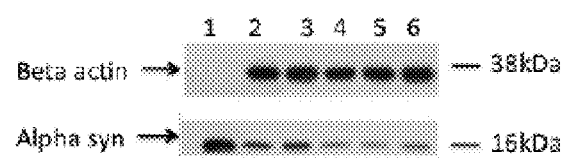
Figure 5:
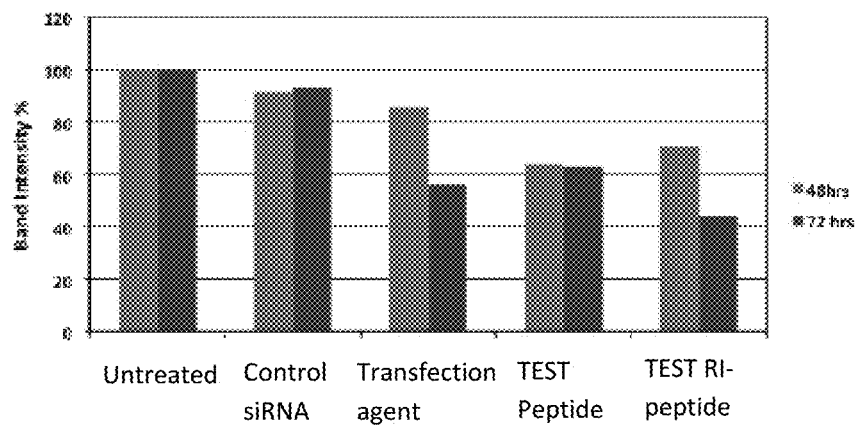
FIG. 5 shows the quantification of each band shown in FIG. 4 by ImageJ software. α-Synuclein expression was normalized by beta-actin. Bars were plotted relative to untransfected cells.

The levels of α-synuclein protein after 48 and 72 hrs were also determined by western blotting. After 48 hrs of transfection TEST-peptide/siRNA and TEST-RI-peptide/siRNA complexes showed a knockdown of 30-40% of α-synuclein protein levels compared to 20% knockdown achieved after transfecting cells with a commercial transfection agent. Furthermore, the levels of α-synuclein expression decreased 72 h post transfection, with upto 60% knockdown of α-synuclein protein levels achieved when the cells were transfected by the peptide/siRNA complexes, compared to only 40% knockdown of α-synuclein protein when the siRNA was transfected with the commercial transfection agent FIG. 4 and FIG. 5.

These results suggest that the TEST-peptide and TEST-RI-peptide are able to deliver functional siRNA to the same or greater extent compared to commercial transfection agents, and are able to decrease α-synuclein expression when complexed to siRNA α-synuclein molecules.

Example 4—Trans-Vascular Delivery of siRNA into CNS

To determine if the peptides can cross the BBB into the CNS and to be able to selectively bind to neurons, the biotinylated peptides were intravenously injected into the tail vein of 16 week month old naive C57BL/6 mice.

200 μg of biotinylated peptides in 0.2 ml of PBS or PBS alone were intravenously injected through the tail veins of 16 week old male C57BL/6 mice (n-5 per group). The animals were sacrificed at different time points post-injection (5 min, 15 min, 30 min, 6 h, 8 h, 24 and 48 h). After which the brains were harvested for immnunofluorescence analysis.

The tissues were processed for immunofluorescence analysis with anti-biotin antibody and detected with an anti-FITC secondary antibody (green) to visualise the immunoreactivity of biotinylated peptide in the tissue sections.

To test the uptake of FITC-siRNA in the brain, peptide/siRNA-FITC complexes (at a peptide to siRNA molar ratio of 60:1) were prepared in 200 µl of 5% glucose. 16 week old naïve mice (n-6 per group) were injected intravenously twice a day, 6 hours apart with the peptides, TEST-peptide or TEST-RI-Peptide, complexed to siRNA labelled with FITC (siRNA-FITC at a molar ratio of 1:60) or with siRNA-FITC alone, at 50 µg of siRNA per mouse per injection.

The BBB permeability of peptides was assessed by histological analysis of the brain. 10 hours after the second injection, animals were anesthetized, perfused with Zamboni's fixative and the brains, liver, kidneys and spleen were collected. The tissues were processed for double immunofluorescent staining with anti-NeuN antibody to detect neurons (detected with rhodamine labelled secondary antibody, (red)) and with an anti-FITC secondary antibody (green) to visualise siRNA-FITC in the sections. FITC fluorescence was observed in neurons with different regions throughout the brain including hippocampus (A) striatum (B) and SNpc (C) only when the siRNA-FITC was complexed with the peptide and not in sections from mice injected with siRNA-FITC alone.

Figure 6A:
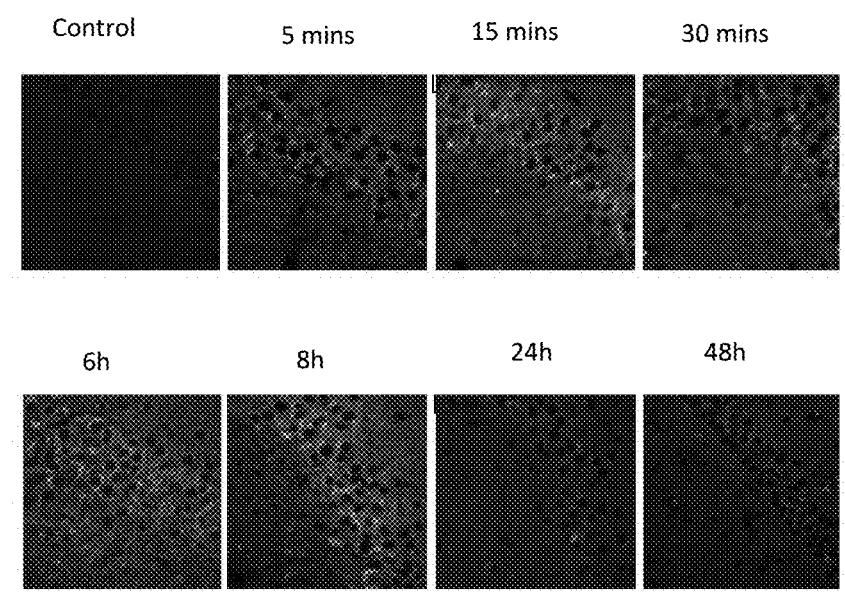
FIGS. 6A, 6B, and 6C show the results from the immunofluorescence analysis of the hippocampus (FIG. 6A), striatum (FIG. 6B), and SNpc (FIG. 6C) from mice injected with a biotin test-peptide (SEQ ID NO:4) solution in PBS or with PBS alone (control) over time.
Figure 6B:
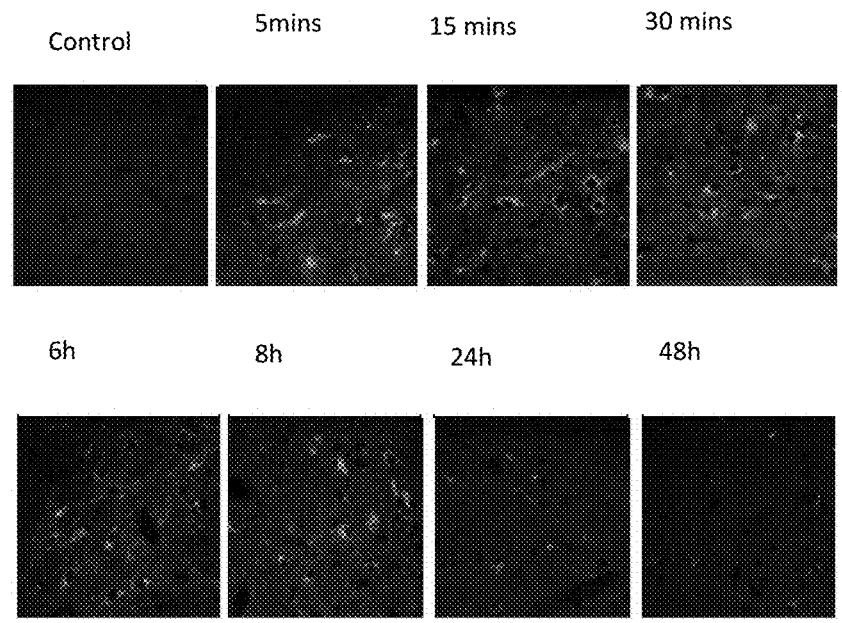
Figure 6C:
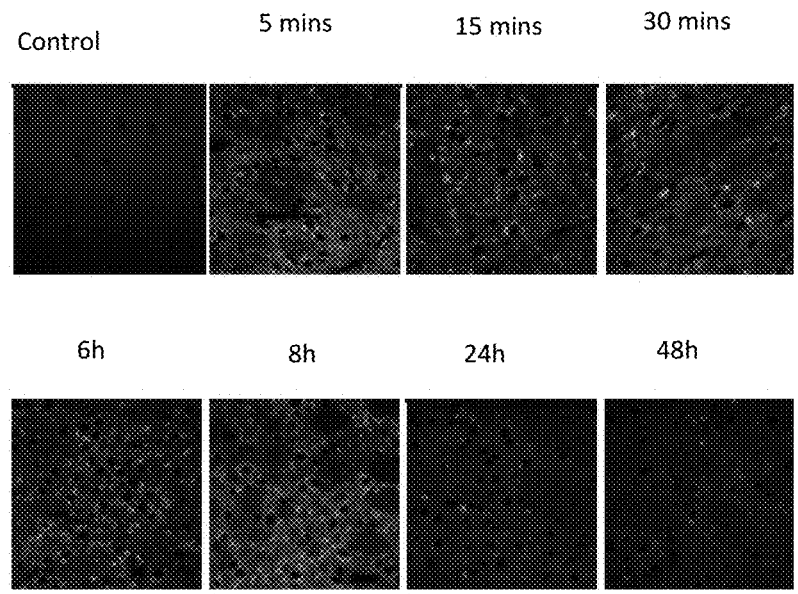

As shown in FIGS. 6A-C, the peptides were detected in different regions of the brain at as early as 5 minutes after intravenous (i.v.) administration demonstrating the ability of the peptides to easily cross the BBB. Furthermore, the peptides remained in the brain tissue for upto 8 hours. Maximum fluorescence signals were observed at 8 h post-injection followed by a gradual decline of signals over time. After 48 hours, very little of the biotin-tagged peptide could be visualized in the brain.

These results indicate that the peptides can efficiently and rapidly cross the BBB, reach neurons within the CNS and be cleared out from the brain within a reasonable time window (~48 hrs), which allows for clinical operation.

Figure 7A:
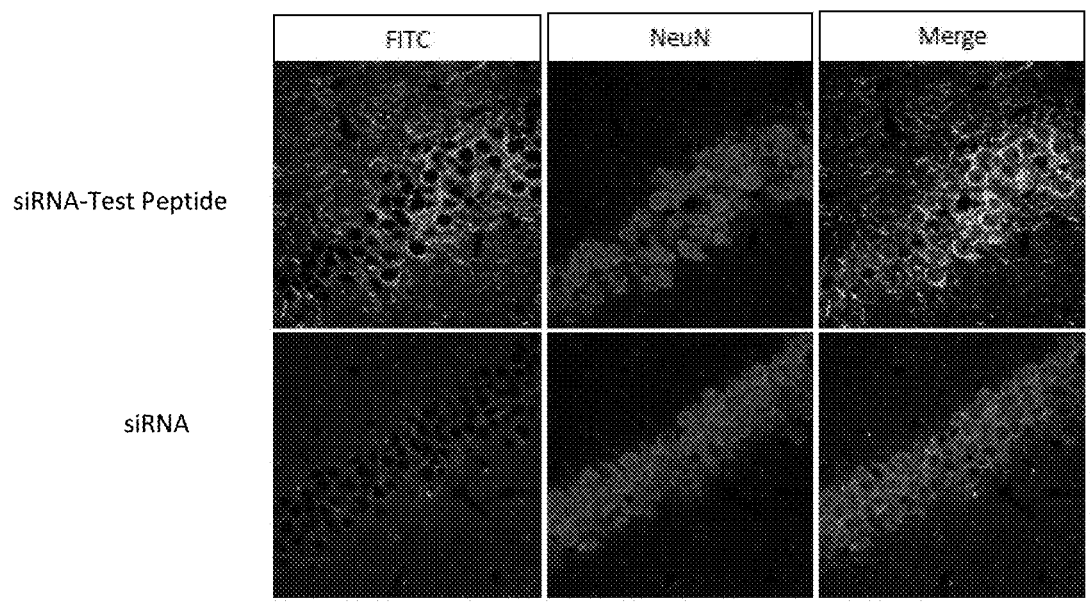
FIGS. 7A, 7B, and 7C show the results from the immunofluorescence analysis of the hippocampus (FIG. 7A), SNpc (FIG. 7B), and striatum (FIG. 7C) from mice injected with the test peptide (SEQ ID NO:4) complexed to siRNA labelled with FITC (siRNA-FITC) or with siRNA-FITC alone (control). The tissues were processed with an anti-NeuN antibody to detect neurons and an anti-FITC secondary antibody to visualise siRNA-FITC in the tissue sections.
Figure 7B:
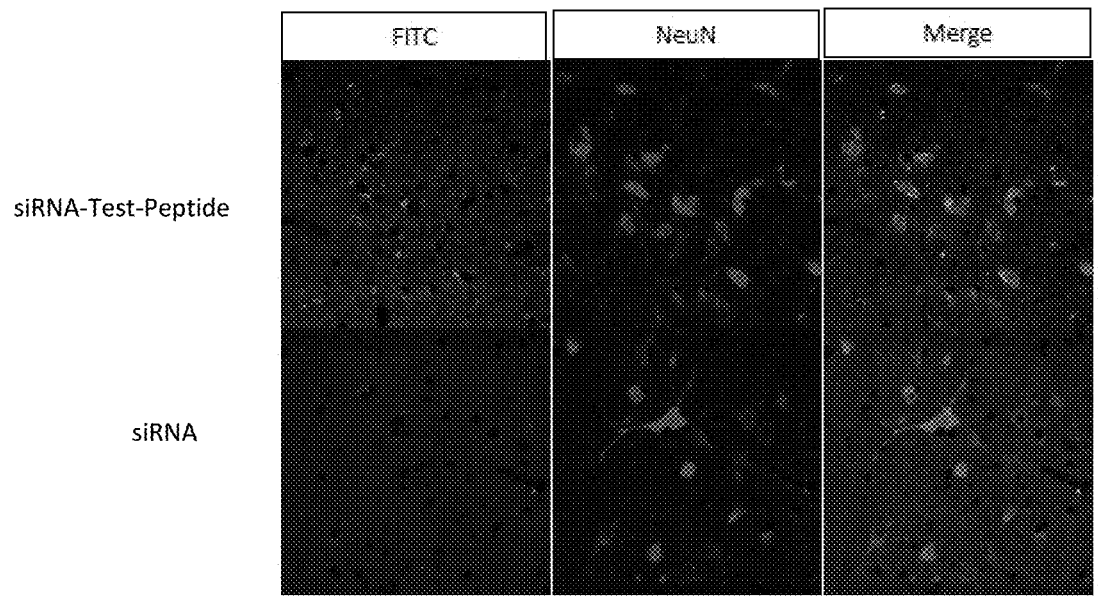
Figure 7C:
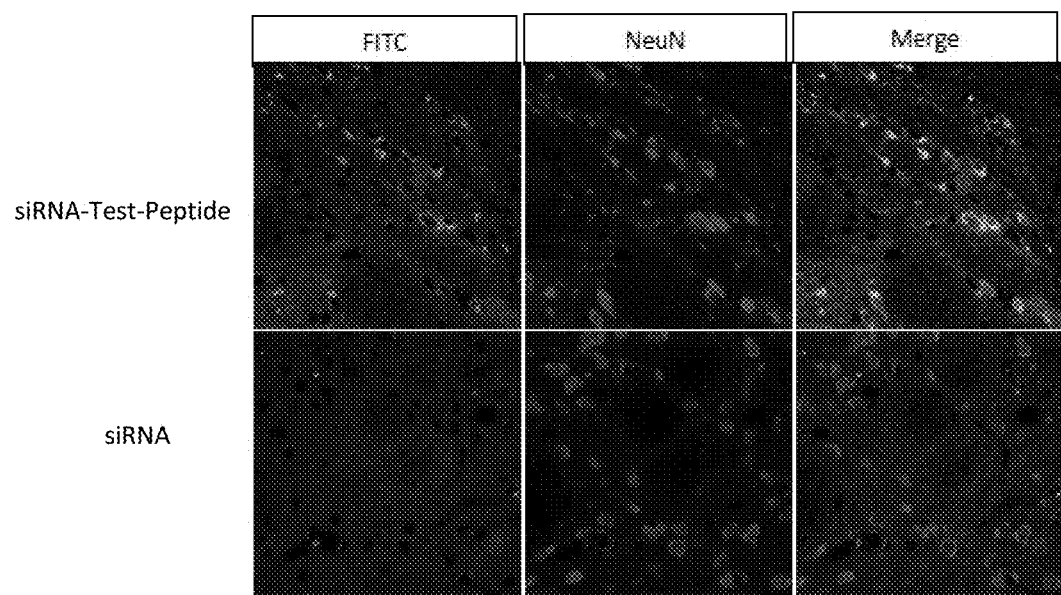

To determine if the peptides can facilitate the delivery of siRNA specifically into neurons within the CNS, naïve mice were injected intravenously with FITC-siRNA complexed to the peptides, or with FITC-siRNA alone after which the brains, liver, kidney and spleen from the injected mice were collected, processed and analysed for the presence of FITC positive staining. The presence of FITC positive neurons in different regions within the brain (FIGS. 7A-C) and the absence of any FITC signal from the liver, kidney and spleen (data not shown) of the injected mice confirmed that the peptides deliver siRNA into neurons within the brain and suggesting the specificity of the peptides in targeting neurons within the CNS.

Furthermore, injection of the TEST-peptide or the TEST-RI-peptide did not elicit an antibody response or result in the production inflammatory cytokines, confirming that these peptides do not generate immunogenicity. To investigate if the peptides induce cytotoxicity, tissue sections from the liver, spleen, kidney and brain of peptide injected mice were analysed by hematoxylin and eosin immunostaining. There was no visible cell death observed in any of these regions confirming the lack of toxicity effect of the peptides on the target tissue or other tissues (data not shown).

Example 5—α-Synuclein Knockdown In Vivo

To test brain tissue specific α-synuclein gene silencing, 16 week old mice were injected with siRNA molecules, designed to target mouse α-synuclein, complexed with the TEST-peptide or TEST-RI-peptide on three consecutive days or with a siRNA/RVG-9R complex (as a positive control). Two days after the final injection the brain, spleen and liver cells of the inject animals were dissected out and analysed by Western blot and ELISA for α-synuclein expression.

α-Synuclein knockdown after intravenous injection of siRNA into mice was analysed by western blotting. Brain lysates from cortex, hippocampus, striatum, cerebellum and midbrain were subjected to electrophoresis on 15% SDS polyacrylamide gels and transferred onto nitrocellulose membranes. The membranes were probed with anti-α-syn antibody (211, Santa Cruz Biotechnology) and β-actin antibody (Santa Cruz Biotechnology). The protein bands were visualized using Super signal west pico chemiluminescent substrate (Pierce) and the band intensities determined using Quantity One-4.1.1 software (Bio-Rad) and Image J.

For ELISA analysis a 384-well ELISA microplate (Nunc MaxiSorp, NUNC) was coated by overnight incubation at 4° C. with anti-α-syn antibody (syn-1, BD Biosciences, 1:2000 dilution) in 200 mM $NaHCO_3$, pH 9.6 (50 µl/well). The plate was washed with PBST and incubated with blocking buffer (100 µl/well) for 2 h at 37° C. After washing, 50 µl/well of recombinant human α-synuclein standards or mouse brain lysates (0.1 mg/ml) were added in triplicates and the plate was incubated at 37° C. for an additional 2.5 h following which, the detection antibody anti-synuclein (FL-140, Santa Cruz Biotechnology, 1:1000 dilution) was added, and the plate was incubated at 37° C. for 1 h. The plate was washed with PBST and then incubated for 1 h at 37° C. with the secondary antibody goat anti-rabbit IgG HRP (Jackson Immunoresearch; 1:10000 dilution). Subsequent to washes with PBST, the plate was incubated with 50 µl/well of SuperSignal ELISA Femto Maximum Sensitivity Substrate (Pierce). The chemiluminescence, in relative light units was measured immediately using a Victor X3 microplate reader.

Figure 10:
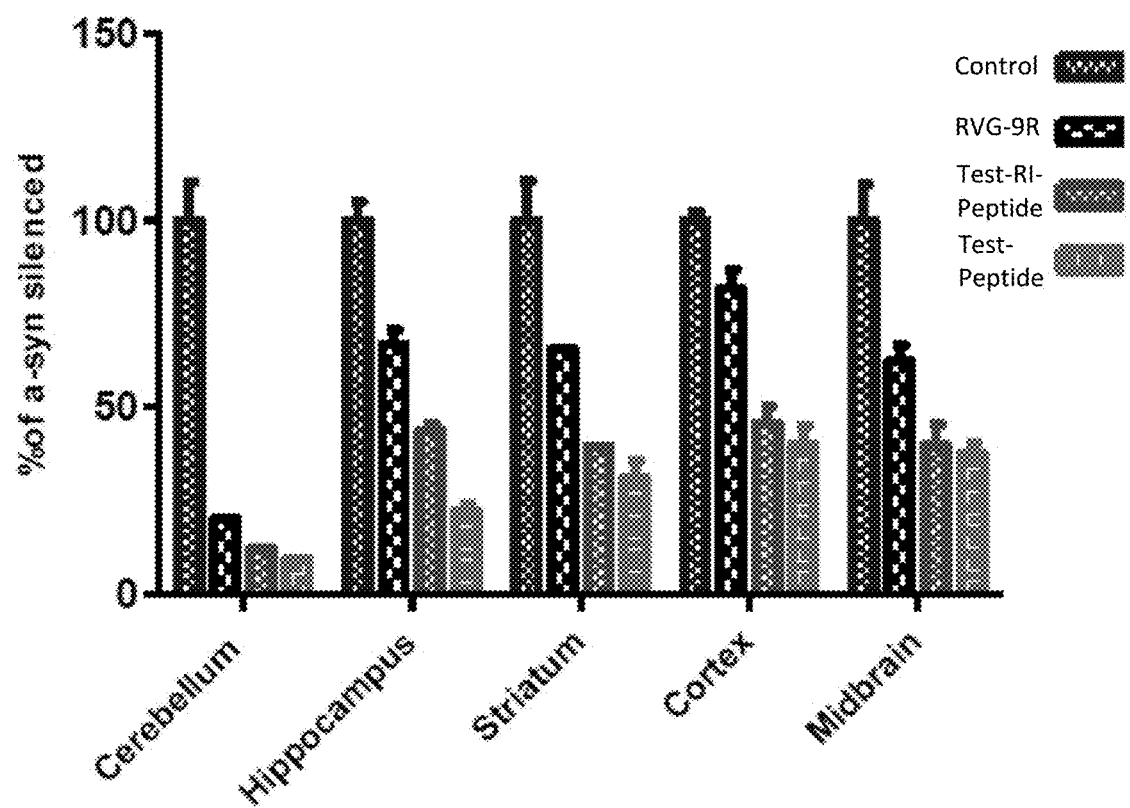
FIG. 10 shows the ELISA results showing the percentage of α-synuclein silenced in different regions of brains (cerebellum, hippocampus, striatum, cortex and midbrain) from mice injected with peptide/siRNA complexes. p<0/0001.

Western blot analysis (FIGS. 9A-9D) and ELISA (FIG. 10) showed there was a decrease in α-synuclein expression after treatment with the siRNA/TEST-peptide and siRNA/TEST-RI-peptide complexes. No downregulation of α-synuclein was observed in the kidney and spleen (results not shown), confirming that the peptides targeted neurons within the brain. The results are also summarised in Table 1:

TABLE 1

| Region | Decrease in levels of α-synuclein protein expression (% of control) | | |
|---|---|---|---|
| | Test-peptide/siRNA | Test-RI-peptide/siRNA | RVG-9r/siRNA |
| Cortex | 60%; $P < 0.01$ (**) | 54%; $P < 0.05$ (*) | 18%; $P > 0.05$ (ns) |
| Hippocampus | 78%; $P < 0.001$ (***) | 56%; $P < 0.05$ (*) | 33%; $P > 0.05$ (ns) |
| Striatum | 69%; $P < 0.01$ () | 60%; $P < 0.01$ () | 34.5%; $P > 0.05$ (ns) |
| Mid-brain | 62%; $P < 0.01$ () | 60%; $P < 0.01$ () | 38%; $P > 0.05$ (ns) |
| Cerebellum | 90%; $P < 0.001$ (*) | 88%; $P < 0.001$ (*) | 80%; $P < 0.001$ (***) |

The results confirmed that siRNA mediated SNCA downregulation was achieved to a greater extent by the Test-peptide and Test-RI-peptide compared to the longer RVG-9r peptide in all regions of the brain analysed. The peptides of the invention were more efficient at silencing α-synuclein in the brain as compared to the longer RVG-9r peptide.

Example 6—Protection of Human M17 Cells from MPTP-Toxicity

It has been reported that neuronal cells in which α-synuclein has been knocked out are resistant to MPTP toxicity. The efficiency of α-synuclein suppression mediated by peptide vectors was tested using the MPTP toxicity model.

The toxicity effect of the peptide-siRNA complexes was assessed by measuring the cellular redox activity with MTT. M17 cells were plated at a density of 4000 cells per well on 96 well plates in 100 µl of OPT-MUM serum free medium. Next day the cells were treated with the TEST-peptide/siRNA or TEST-RI-peptide/siRNA complexes, and after 6 h 10% fetal bovine serum was added to the media, after which the cells were incubated for another 72 h. 10 µl of MTT (6 mg/ml) in PBS was added to the cells at a final concentration of 0.5 mg/ml, and the incubation was continued for another 4.5 h. 100 µl/well of cell lysis buffer (15% SDS, 50% N,N-dimethylformamide, pH 4.7) was added to the cells and incubated overnight at 37° C. in a humidified incubator. Absorbance values at 590 nm were determined with a plate reader. To measure the effect of MPTP toxicity, the 3-(4,5-dimethylthiazol-2-yl)-2,5-diphenyltetrazolium bromide (MTT) assay was performed after exposing the cells to 2.5 mM MPTP in serum free medium for 6 h.

Figure 8A:
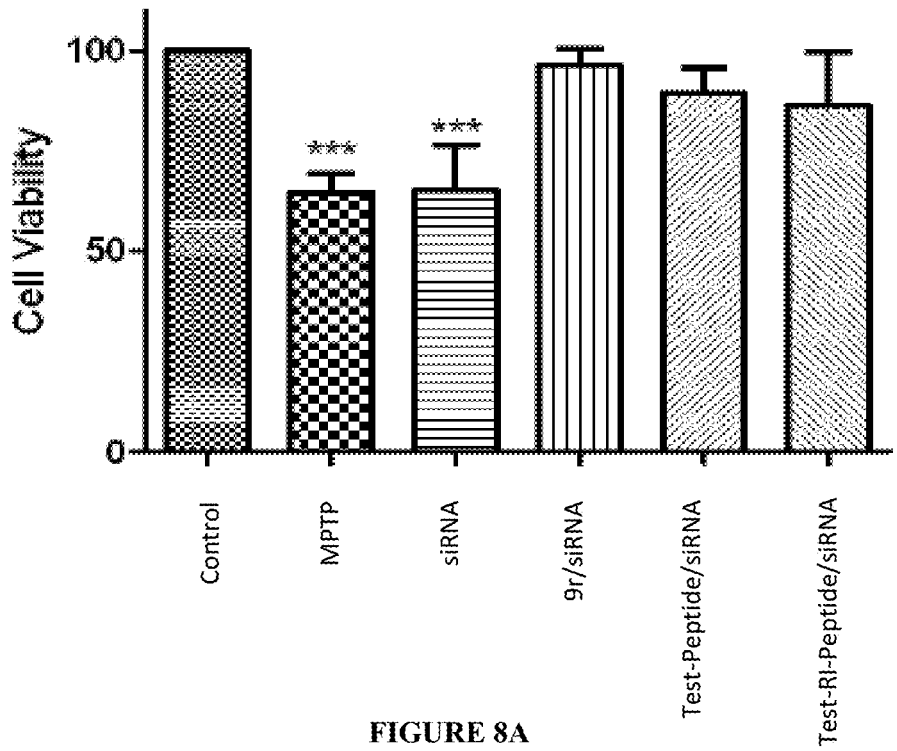
FIGS. 8A and 8B show the results of (FIG. 8A) the cell viability MTT assay of M17 cells stably expressing wild type α-synuclein transfected with peptide-siRNA complexes, siRNA using commercial media (positive control), a scrambled siRNA (negative control) or with MPTP alone (One-way anova, siRNA effect, P<0.0001) and (FIG. 8B) the cell viability MTT assay of M17 cells incubated with complexes of siRNA with peptides, peptides alone or siRNA alone ("6r," "9r," and "12r" are disclosed as SEQ ID NOS 13, 9, and 14, respectively)

A 6 h exposure to 2.5 mM of MPTP resulted in a 40% reduction of MTT uptake compared to control cells, which was almost completely prevented by treatment with either RVG9r/siRNA, TEST-peptide/siRNA or TEST-RI-peptide/siRNA complexes. Furthermore, there was no apparent protection from MPTP-induced cytotoxicity when the cells were treated with siRNA alone (FIG. 8A).

M17 cells were significantly protected by α-synuclein knockdown from MPTP exposure.

Figure 8B:
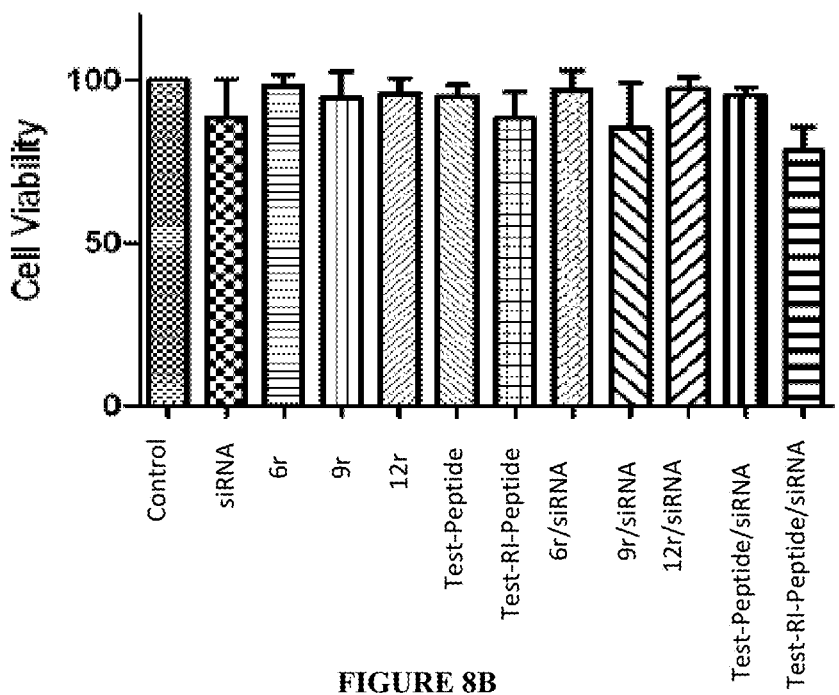
Figure 9A:
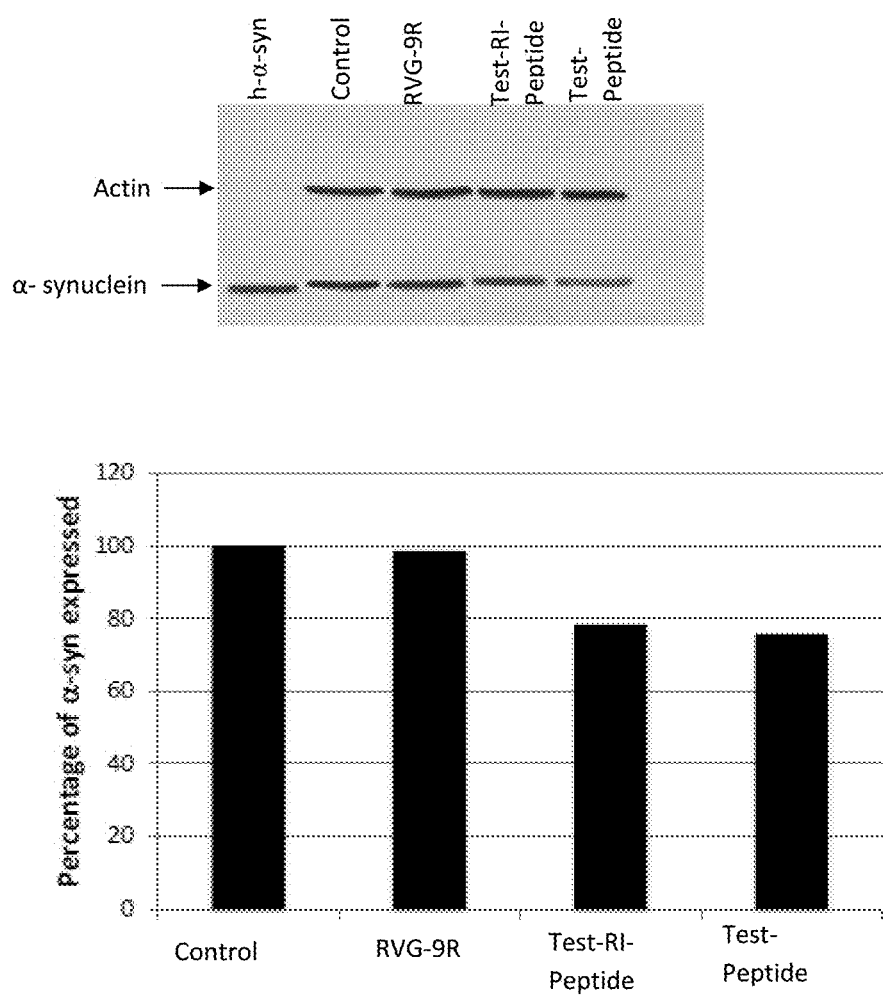
FIGS. 9A, 9B, 9C, and 9D show the western plot analysis to test gene silencing in different regions of the brain from mice injected with peptide/siRNA complexes: hippocampus (FIG. 9A), midbrain (FIG. 9B), cerebellum (FIG. 9C), and cortex (FIG. 9D)
Figure 9B:
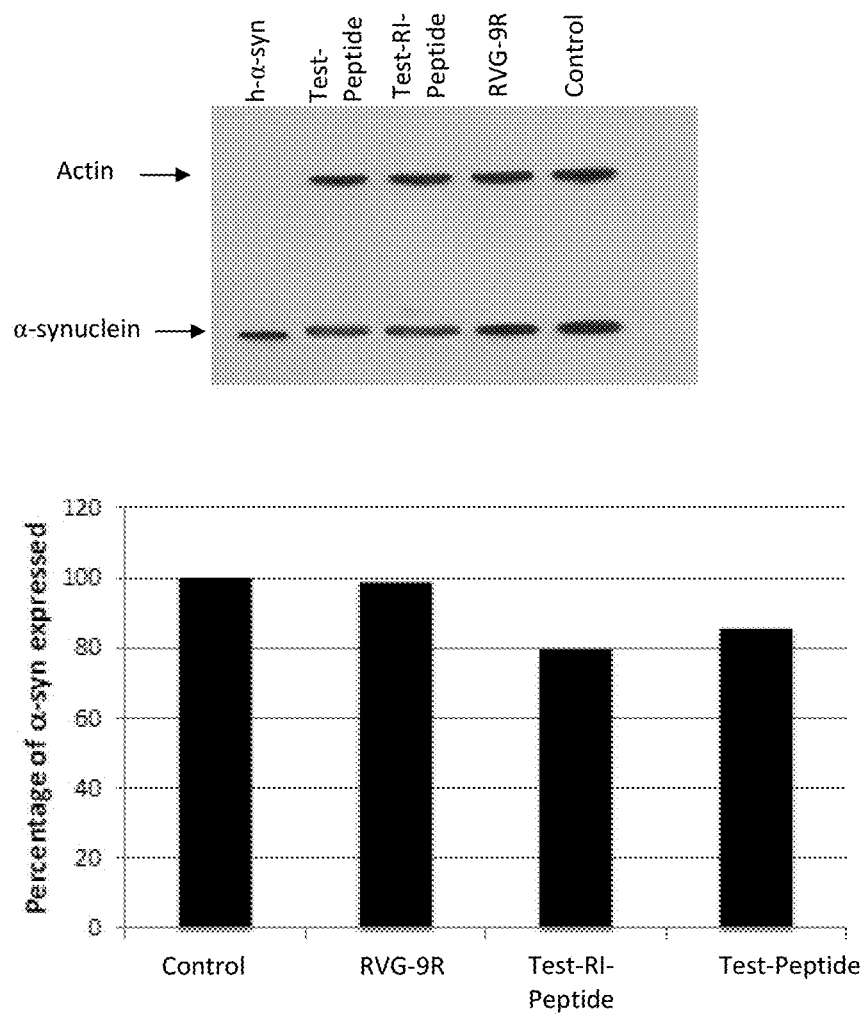
Figure 9C:
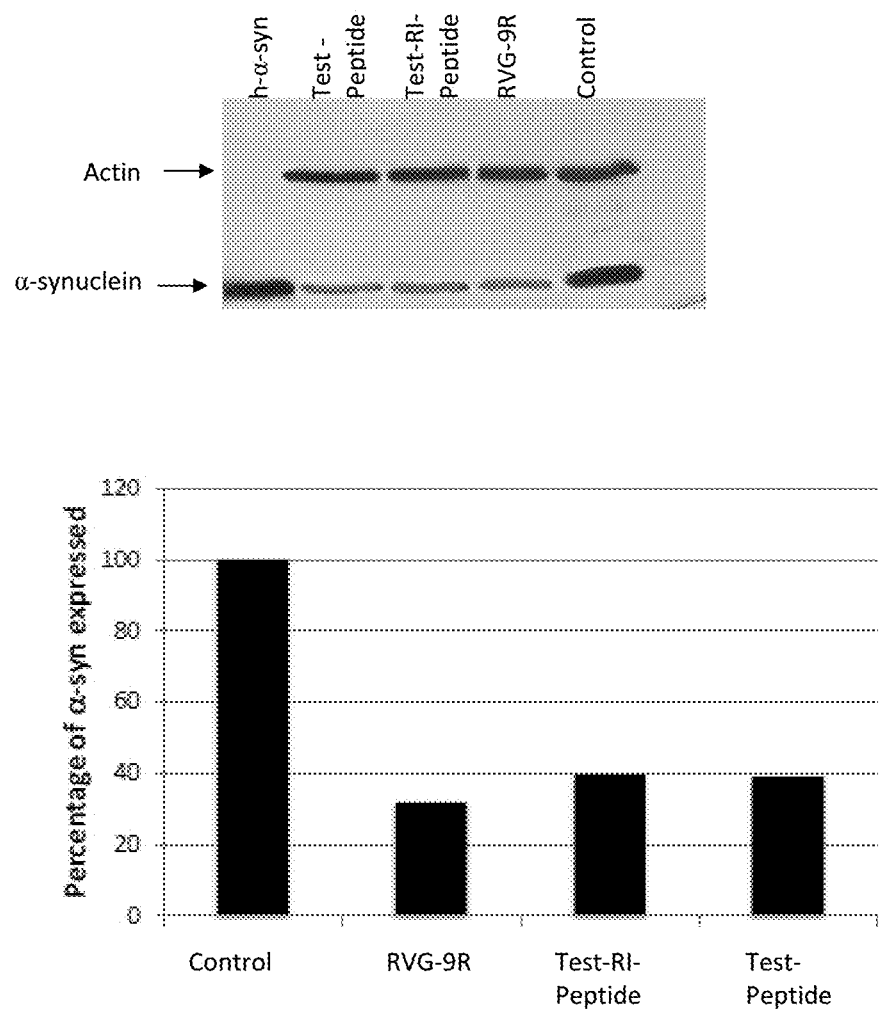
Figure 9D:
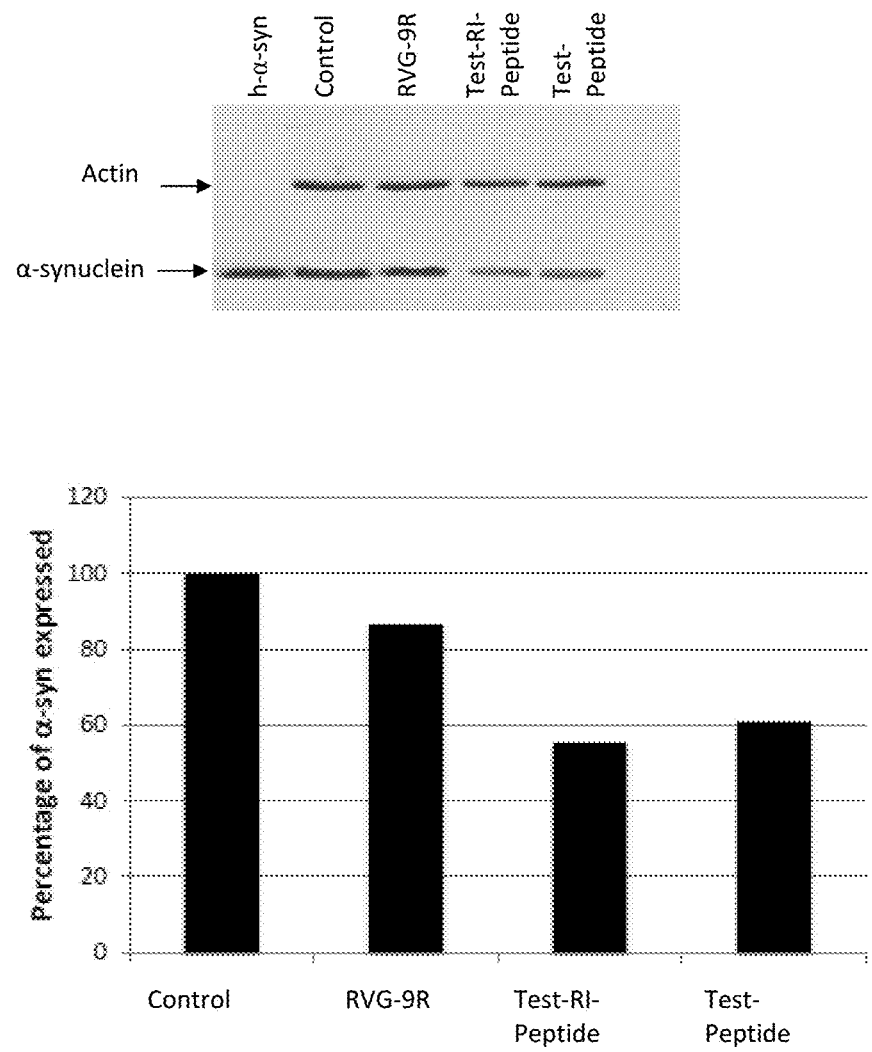

To rule out the possibility that the observed cell death could be a result of α-synuclein downregulation, the effect of α-synuclein depletion on cell viability was analysed. After 72 hrs of transfection, there was no significant difference in cell viability in cells treated with peptide/siRNA complexes, siRNA alone, peptides alone or untransfected cells (FIG. 8B).

Example 7—Protection of Mice from MPTP-Toxicity In Vivo with Peptide-siRNA Complexes Targeting α-Synuclein An MPTP model was used to test that the peptides can deliver α-synuclein siRNA into the brain, downregulate α-synuclein and thus protect dopaminergic neurons against of MPTP induced toxicity. 30 male C57BL/6 mice of 8-16 weeks of age weighing 23-28 were randomly divided into 5 groups of six as follows:
Group 1: control
Group 2: MPTP
Group 3: MPTP+siRNA/RVG-9R
Group 4: MPTP+siRNA/TEST-peptide
Group 5: MPTP+siRNA/TEST-RI-peptide Groups 3-5 were intravenously injected with siRNA/peptide complexes as indicated for three consecutive days whereas groups 1 and 2 were injected with saline. Two days after the last injection, groups 2-5 were intraperitoneally injected with MPTP (16 mg free base/kilo body weight; MPTP-HCl; Sigma-Aldrich) four times over a single day, 2 hours apart. Mice used as control received an equivalent volume of saline. Two more siRNA/peptide injections were given to mice from groups 3-5 over the next 4 days and on the fifth day after MPTP injection, the mice were subjected to behaviour tests and later sacrificed for immunohistochemical analysis. MPTP handling and safety measures were in accordance with published recommendations (Jackson-Lewis, 2007, Protocol for the MPTP mouse model of Parkinson's disease).

Rotarod performance was assessed 5 days after MPTP intoxication. The 8-16 week old male C57BL/6 mice were briefly pre-trained for 3 weeks on an automated 4-lane rotarod unit (Rotamex-5, Columbus Instruments, Columbus, Ohio; Lane width, 95 mm, rod diameter 30 mm) that could be set on fixed or accelerating speed. For the fixed speed protocol mice were placed on the rod and tested at 20 rpm for a maximum of 60 s. For the accelerated speed protocol, mice were subjected to an incrementally increasing speed from 1 to 20 rpm over a period of 5 min. For both protocols, the length of time that each animal was able to stay on the rod was recorded as the latency to fall, registered automatically by scanning infrared beam sensors that monitor the animal's absence from the rod assembly. At the end of the training period, each animal underwent 3 trials and the average of the three runs was recorded as their performance before treatment.

Four groups of MPTP-treated mice underwent fixed and accelerated speed rotarod test 5 days after MPTP intoxication and the latency to fall off the rotarod was recorded. Six control mice that were injected with saline were used to compare the effect of MPTP treatment on rotarod performance. The average of 3 trials per protocol was recorded as their performance after treatment.

For immunofluorescence analysis to visualize biotinylated peptides or FITC labelled siRNA in the CNS of injected mice, the mice were transcardially perfused with Zamboni's fixative. The brain, spleen, kidney and liver were harvested, post-fixed for 4 h in the same fixative and cryoprotected overnight with 30% sucrose solution. The organs were rapidly frozen and sectioned coronally into 40 µm slices that were stored in 0.1M PBS with 0.01% sodium azide at 4° C. The sections were washed in PBS, blocked with 1% bovine serum albumin for 30 min to prevent non-specific antibody binding and incubated overnight at 4° C. with the primary antibodies rabbit anti biotin (1:15000, Abcam) to visualize biotinylated peptides or rabbit anti-FITC (1:500, AbD serotec) and mouse anti-NeuN (1:750, Millipore) to visualize FITC labelled siRNA specifically in neurons. The sections were then incubated with the secondary antibodies (rhodamine conjugated anti-mouse, 1:500, Jackson Immunoresearch and FITC conjugated anti-rabbit, 1:500, Jackson Immunoresearch) for 2 h at room temperature and mounted with 10% glycerol subsequent to washes in PBS and distilled water.

To ascertain that the protection observed in mice treated with siRNA/peptide complexes was due to decreased lesion caused by MPTP intoxication, the mice brains were analysed by tyrosine hydroxylase immunohistochemistry. The mice were anesthetized and transcardially perfused with 0.1M PBS. The brains were removed and post-fixed for 48 h in 4% paraformaldehyde in 0.1M phosphate buffer. Fixed tissues were then processed by dehydration through a graded series of ethanol, cleared in xylene, embedded in paraffin blocks and sectioned into 8 µm coronal slices. The sections were de-paraffinized in two xylene washes, and then rehydrated in decreasing concentrations of ethanol followed by two washes with distilled water. Antigen retrieval was carried out by boiling the sections in sodium-citrate buffer (pH 6). Following washes with 0.1M PBS, the sections were incubated in 3% $H_2O_2$ for 20 min to inhibit endogenous peroxidase activity. After blocking with 5% normal goat serum (Sigma), the sections were incubated overnight at 4° C. with anti-TH (1:500, Millipore), followed by incubation with biotin-conjugated donkey anti-mouse secondary antibody (1:500, Jackson Immunoresearch) for 2 h at room temperature. After three washes in PBS, the sections were incubated in avidin-biotin complex (Vectastain Elite kit, Vector Laboratories, UK) for 1 h at room temperature and later with the DAB substrate (Vectastain Elite kit, Vector Laboratories, UK). The development of a dark brown reaction product was monitored by eye and stopped with several washes of distilled water.

The number of TH positive neurons in the SNpc from control, and the MPTP treated groups were evaluated. To determine the loss of dopaminergic neurons in the substantia nigra pars compacta, the total number of TH-positive cells at four different depths (−2.92, −3.08, −3.16 and −3.28 mm of bregma) within the SN were counted and an average of the four regions was calculated for each brain analysed. The counting was carried out manually by a researcher blinded to the treatment schedule. To avoid double counting of neurons with unusual shapes, TH positive cells were counted only when their nuclei were optimally visualized. Loss of striatal fibres was evaluated by measuring the optical density of TH immunoreactive fibres in the striatum using ImageJ software. The optical density of TH-ir fibres at three different regions within the striatum was measured for each animal and an average of the 3 areas was calculated. The optical density of the overlying corpus callosum was taken as a background measure and subtracted from the value generated from the striatum.

Figure 11A:
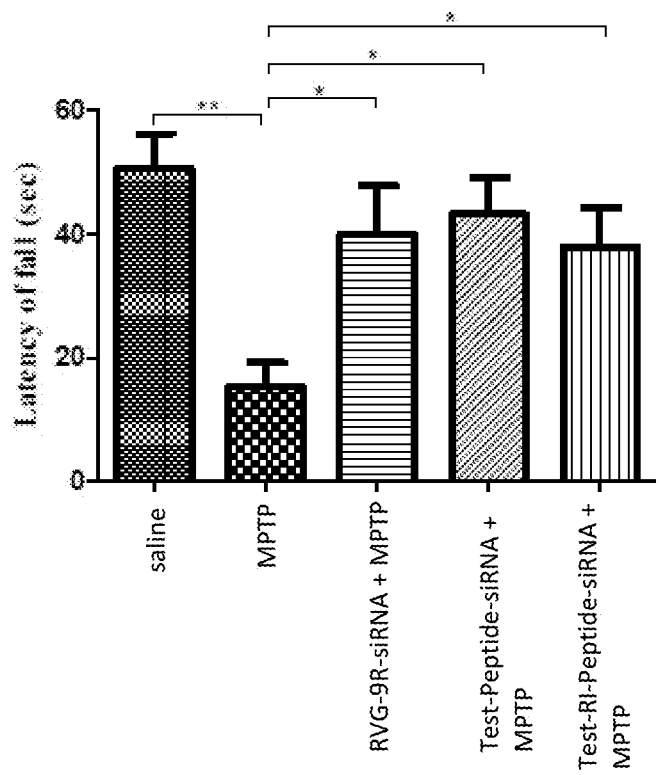
FIGS. 11A and 11B show the results of the behaviour analysis of mice treated with MTPT and peptide-siRNA complexes. Rotarod performance was assessed on a (FIG. 11A) fixed speed rotarod, p=0.0037 () by one-way ANOVA for multiple comparison ( p<0.01, *p<0.05 by Newman-Kauls post hoc analysis to test individual groups against MPTP treated group) and on a (FIG. 11B) accelerated rotarod p=0.0183 (*) by one-way ANOVA for multiple comparison (*p<0.05 by Newman-Kauls post hoc analysis to test individual groups against MPTP treated group). Data are represented as means±SEM.

To assess the neurological deficits in mice after treatment with MPTP and the efficacy of the therapeutic treatment, a fixed speed rotarod test was performed. Mice that had been treated with MPTP alone showed a significant reduction in performance at the rotarod and fell off the rod within one-third of the total time assayed (60 sec) (30% performance compared to control mice, $P<0.01$). Mice that had been treated with the siRNA/peptide complexes managed to stay on the rod for a longer duration and their performance was comparable to that of saline treated controls (Test-peptide: 85%; $P<0.05$, Test-RI-peptide: 75%; $P<0.05$, and RVG-9r: 78%; $P<0.05$, n=8/group; FIG. 11A).

Figure 11B:
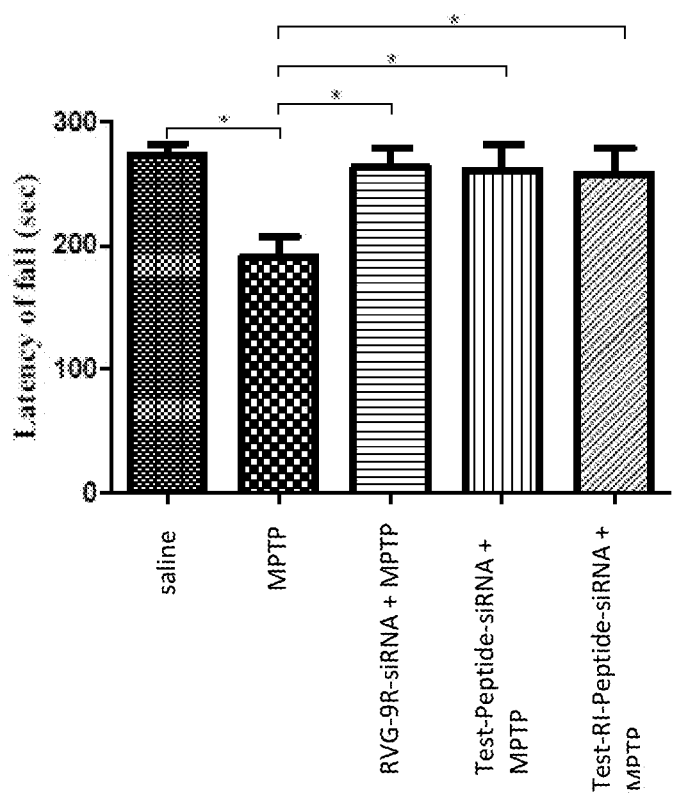

An accelerated rotarod test was also performed, which correlates motor deficits with the size of lesions (Monville et al, 2006). MPTP treated mice showed a significant reduction in performance (69% performance compared to control group, $P<0.05$), although the decrease in performance was less severe than that observed by the fixed speed rotarod test, while the siRNA/peptide treated groups showed performance levels nearing that of the control group (Test-peptide: 94%; $P<0.05$, Test-RI-peptide: 95%; $P<0.05$, and RVG-9r: 96%; $P<0.05$, n=8/group) FIG. 11B).

Figure 12A:
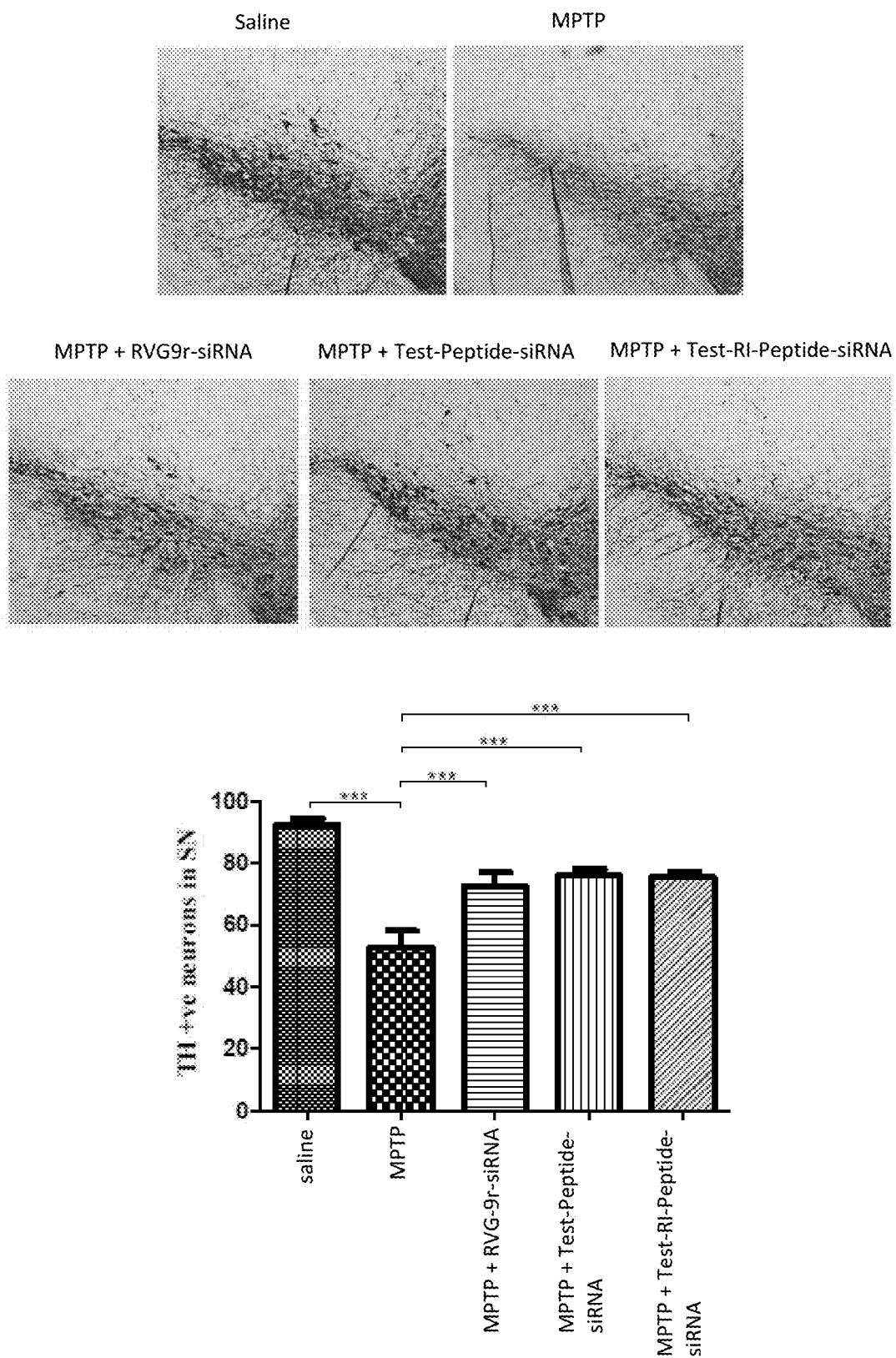

To ascertain that the protection observed in mice treated with siRNA/peptide complexes was due to decreased lesion caused by MPTP intoxication, the mice brains were analysed by immunohistochemistry. MPTP treated mice retained 57% of TH positive neurons in the SNpc compared to the control group ($P<0.001$). The groups that had been treated with MPTP and protected with the siRNA/peptide complexes showed a significant protection of dopaminergic neuronal loos (C2-9r: 80% TH positive neurons compared to control; $P<0.001$, RI-C2-9r: 82%; $P<0.001$, RVG-9r: 79%; $P<0.001$) FIG. 12A.

Figure 12B:
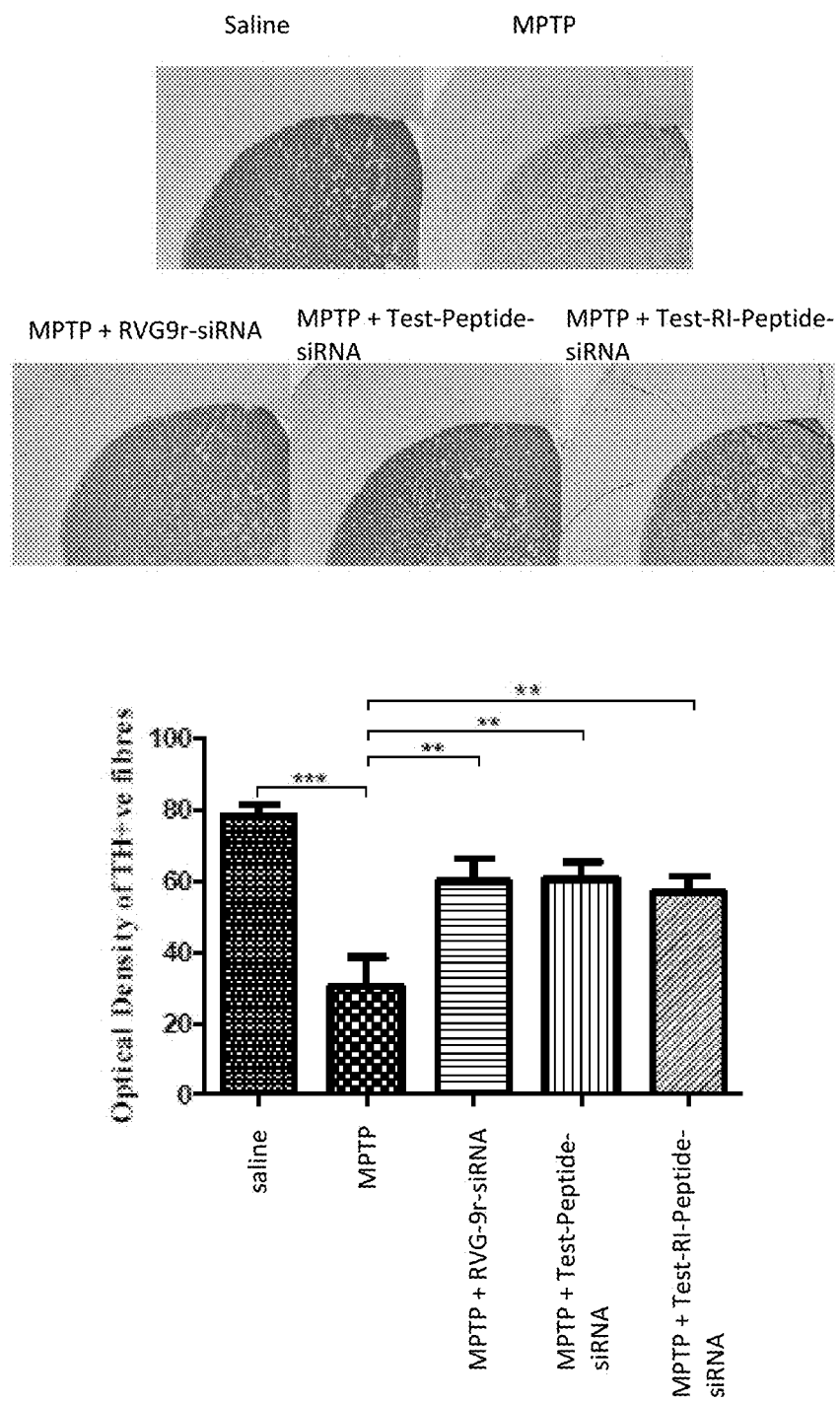
(FIG. 12B) Means±SEM for 4-5 mice per group. p=0.0005 (*) by one-way ANOVA for multiple comparison. *p<0.001, **p<0.01, *p<0.05 by Newman-Kauls post-hoc analysis to test individual groups against MPTP treated group.

Axons from the dopaminergic neurons in the substantia nigra project into the striatum to maintain dopaminergic transmission. Thus, an increase in cell death at the SN would result in a decrease in the amount of axonal fibres in the striatum. To quantify this, the striatum from the different groups were stained for TH immunopositive fibres. A loss of TH-ir fibres in the MPTP treated group was observed (43% TH-ir fibres compared to the control group; $P<0.001$) whereas the siRNA/peptide treated groups showed a significant protection of striatal fibres (C2-9r: 77% TH-ir fibres compared to saline treated control group; $P<0.01$, RI-C2-9r: 72%; $P<0.01$, RVG-9r: 76%; $P<0.001$; FIG. 12B).

Example 8—Immunogenicity Study

Mice were injected intravenously with 50 µg of siRNA complexed with either the Test-Peptide or Test-RI Peptide vectors, with the peptide vector alone or with PBS as negative control for three consecutive days, and then on every alternate day for 14 days. From the 4th day of siRNA injection, MPTP was intraperitonially injected into mice every day for 14 days (45 mg/kg body weight, measured as free base). To detect the presence of antibodies to the Test-Peptide or Test-RI-peptide, serum was collected from the mice on day 21 and serial double dilution (1:100 followed by 10 dilutions) of the sera was incubated in 384 well microtitre plate coated with either Test-Peptide or Test-RI-peptide (50 ng/well). The bound antibody was detected with a goat anti-mouse Ig-HRP conjugate.

Figure 14A:
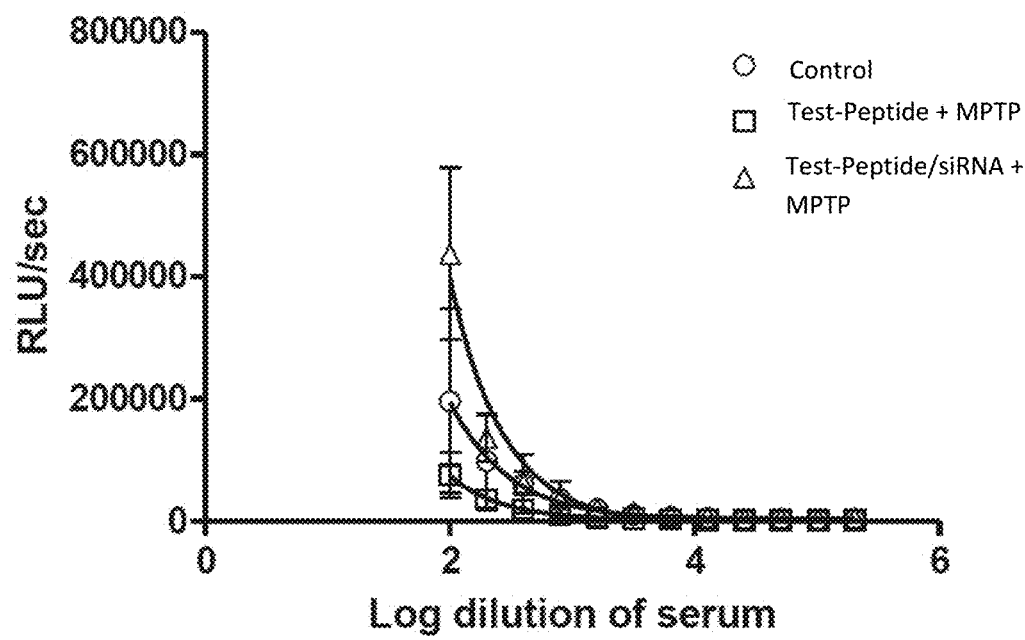
FIGS. 14A and 14B show the results of the immunogenicity test. Mice were injected intravenously with peptide/siRNA complexes or with PBS as negative control. Serum samples collected were tested for the presence of antibodies to Test-peptide (FIG. 14A) or Test-RI-peptide (FIG. 14B) by ELISA.
Figure 14B:
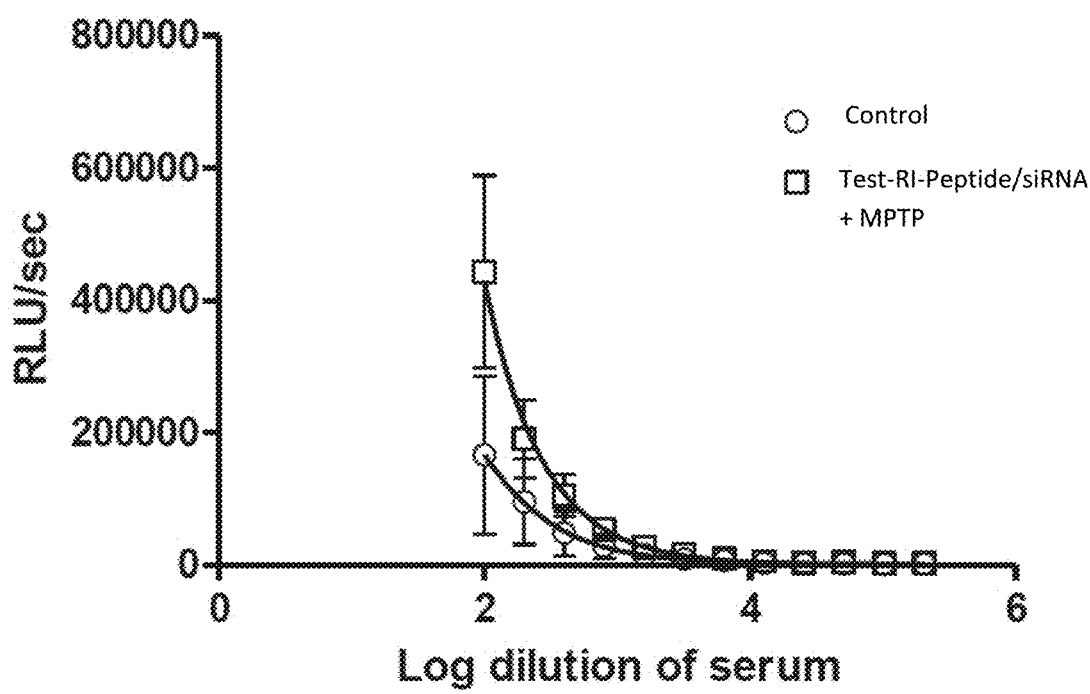

Injection of the Test-peptide or Test-RI-Peptide did not elicit an antibody response, FIG. 14. No significant differences were observed in the immune response between control and peptide treated groups. The small size of the peptides renders them non-immunogenic.

These results suggest that the peptides of the invention would be suitable as delivery vehicles of therapeutic agents, such as siRNA in gene therapy, across the BBB for the treatment of central nervous system disorders. In particular the results suggest that the delivery peptides of the invention can used for delivering siRNA targeting α-synuclein into the CNS for the treatment of Parkinson's disease and other central nervous diseases.

CITATIONS

Monville C, Torres E M, Dunnett S B (2006) Comparison of incremental and accelerating protocols of the rotarod test for the assessment of motor deficits in the 6-OHDA model, Journal of Neuroscience Methods vol. 158(2) p 219-223.

Kumar P, Wu H, McBride J L, Jung K E, Kim M H, Davidson B L, Lee S K, Shankar P, Manjunath N (2007) Transvascular delivery of small interfering RNA to the central nervous system, Nature vol. 448(7149) p 39-43

Zimmerman T S, Lee A C, Akinc A, Bramlage B, Bumcrot D (2006) RNAi-mediated gene silencing in non-human primates, Nature vol 441(7089) p 111-114

The invention claimed is:

1. A peptide consists of the structure:
   $A^1$-B—C or C-B-$A^2$, wherein B is optionally present or absent; and wherein
   $A^1$ comprises the sequence CDIFTNSRGK (SEQ ID NO:2);
   $A^2$ comprises the sequence kGrsntfidc (SEQ ID NO:3);
   B is a linker sequence; and
   C is a cell penetrating peptide (CPP) sequence, wherein the cell penetrating peptide sequence is a polymeric arginine residue sequence,
   wherein $A^1$ and $A^2$ consists of a length of less than 15 residues and
   wherein, if present, the linker sequence consists of a plurality of glycine or sarcosine residues.

2. The peptide according to claim 1 wherein the peptide consists of the sequence of CDIFTNSRGKGGGGrrrrrrrrr (SED ID NO:4).

3. The peptide according to claim 1 wherein the peptide consists of the sequence rrrrrrrrr-Sar-Sar-Sar-Sar-kGrsntfidc (SED ID NO:5).

4. The peptide according to claim 1 further comprising the linker sequence.

5. The peptide according to claim 1 wherein the cell penetrating peptide sequence is a 9 arginine residue sequence (SEQ ID NO: 9).

6. A pharmaceutical composition comprising the peptide according to claim 1, an agent associated with the peptide, and pharmaceutically acceptable carrier or diluent, wherein the agent is an α-synuclein siRNA.

7. A composition comprising the peptide according to claim 1 and an agent associated with the peptide.

8. The composition according to claim 7 wherein the agent is a nucleic acid.

9. The composition according to claim 7 wherein the agent is RNA and is selected from the group consisting of siRNA, mRNA, tRNA, miRNA, shRNA or combinations thereof.

10. The composition according to claim 7 when the agent is an α-synuclein siRNA molecule.

11. The composition according to claim 7 wherein the agent is an siRNA molecule having the sequence of SEQ ID NO: 6.

12. A method for reducing alpha-synuclein in a subject having Parkinson's disease, the method comprising administering to the subject a composition according to claim 7, wherein the peptide is associated with a therapeutic agent, wherein the therapeutic agent is an α-synuclein siRNA.

13. A method for delivering an agent to a cell, the method comprising contacting the cell with a composition comprising the peptide according to claim 1 and the agent associated with the peptide, wherein the agent is a nucleic acid.

14. The method according to claim 13 wherein the cell is a central nervous system cell.

15. The method according to claim 13 wherein the cell is selected from a neuron or glial cell.

16. The method according to claim 13 wherein the cell is present in a subject.

17. The method according to claim 13 comprising administering the composition to the cell by intranasal, subcutaneous, parenteral, intrathecal, intracranial, intravenous or oral administration.

* * * * *